United States Patent [19]

Waldman

[11] Patent Number: 6,087,109
[45] Date of Patent: *Jul. 11, 2000

[54] COMPOSITIONS THAT SPECIFICALLY BIND TO COLORECTAL CANCER CELLS AND METHODS OF USING THE SAME

[75] Inventor: Scott A. Waldman, Ardmore, Pa.

[73] Assignee: Thomas Jefferson University, Philadelphia, Pa.

[ * ] Notice: This patent is subject to a terminal disclaimer.

[21] Appl. No.: 09/193,997

[22] Filed: Nov. 17, 1998

Related U.S. Application Data

[63] Continuation of application No. 08/467,920, Jun. 6, 1995, Pat. No. 5,962,220, which is a continuation-in-part of application No. 08/141,892, Oct. 26, 1993, Pat. No. 5,518,888.

[51] Int. Cl.$^7$ .................................................. C12Q 1/68
[52] U.S. Cl. ............................ 435/6; 536/25.3; 530/350
[58] Field of Search ......................... 536/25.3; 530/350; 435/6

[56] References Cited

U.S. PATENT DOCUMENTS

| | | | |
|---|---|---|---|
| 4,584,268 | 4/1986 | Ceriani et al. | 435/7 |
| 4,601,896 | 7/1986 | Nugent | 424/36 |
| 4,729,893 | 3/1988 | Letcher et al. | 424/98 |
| 4,849,227 | 7/1989 | Cho | 424/498 |
| 5,087,616 | 2/1992 | Myers et al. | 514/21 |
| 5,160,723 | 11/1992 | Welt et al. | 424/1.69 |
| 5,166,320 | 11/1992 | Wu et al. | 530/395 |
| 5,237,051 | 8/1993 | Garbers et al. | 530/350 |
| 5,271,961 | 12/1993 | Mathiowitz et al. | 427/213.31 |
| 5,330,892 | 7/1994 | Vogelstein et al. | 435/6 |
| 5,350,741 | 9/1994 | Takada | 514/3 |
| 5,352,775 | 10/1994 | Albertsen et al. | 536/23.1 |
| 5,399,347 | 3/1995 | Trentham et al. | 424/184.1 |
| 5,443,816 | 8/1995 | Zamora et al. | 424/1.69 |
| 5,518,888 | 5/1996 | Waldman | 435/7.23 |
| 5,585,479 | 12/1996 | Hoke et al. | 536/24.5 |
| 5,601,990 | 2/1997 | Waldman | 435/7.23 |

OTHER PUBLICATIONS

Almenoff et al., "Ligand–based Histochemical Localization and Capture of Cells Expressing Heat–Stable Enterotoxin Receptors", *Molecular Microbiology*, 1993, 8, 865–873 903.

Barchel et al., "Radioimaging and Radiiotherapy" New York, 1983.

Bjorn et al., "Antibody–Pseudomonas Exotoxin A Conjugates Cytotoxic to Human Breat Cancer Cells In Vitro", *Cancer Res.*, 1986, 46, 3262–3267.

Bjorn et al., "Evaluation of Monoclonal Antibodies for the Development of Breast Cancer Immunotoxins", *Cancer Res.*, 1985, 45, 1214–1221.

Bodansky et al., "Peptide Synthesis", John Wiley and Sons, 2d Ed., 1976.

Burgess et al., "Biological Evaluation of a Methanol–Soluble, Heat–Stable *Escherichia coli* Enterotoxin in Infant Mice, Pigs, Rabbits, and Calves", *Infection and Immunity*, 1978, 21, 526–531.

Cawley et al., "Epidermal Growth Factor–Toxin A Chain Conjugates: EGF–Ricin A is a Potent Toxin While EGF–Diphtheria Fragment A is Nontoxic", *Cell*, 1980, 22, 563–570.

Chan et al., "Amino Acid Sequence of Heat–stable Enterotoxin Produced by *Escherichia coli* Pathogenic for Man", *J. Biol. Chem.*, 1981, 256, 7744–7746.

Chung et al., "Enzymatically Active Peptide from the Adenosine Diphosphate–Ribosylating Toxin of *pseudomonas Aeruginosa*" *Infection and Immunity*, 1977, 16, 832–841.

Cohen, M., et al., "Receptors for *Escherichia coli* Heat Stable Enterotoxin in Human Intestine and in a Human Intestinal Cell Line (Caco–2)", *J. Cellular Physiol.*, 1993, 156, 138–144.

Corstens et al., "Chemotactic Peptides: New Locomotion for Imaging Infection?" *J. Nucl. Med.*, 1991, 32(3), 491–494.

Cumber et al., "Preparation of Antibody–Toxin Conjugates", *Methods in Enzymology*, 1985, 112, 207–225.

Currie et al., "Guanylin: An Endogenous Activator of Intestinal Guanylate Cyclase", *Proc. Natl. Acad. Sci. USA*, 1992, 89, 947–951.

de Sauvage, F. et al., "Primary Structure and Functional Expression of the Human Receptor for *Escherichia coli* Heat–stable Enterotoxin", *J. Biol. Chem.*, 1991, 266, 17912–17918.

Dreyfus et al, "Chemical Properties of Heat–Stable Enterotoxins Produced by Enterotoxigenic *Escherichia Coli* of Different Host Origins", *Infection and Immunity*, 1983, 42, 539–548.

Eckelman et al., "Comparison of $^{99m}$Tc and $^{111}$In Labeling of Conjugated Antibodies", *Nucl. Med. Biol.*, 1986, 13, 335–343.

Evans et al., "Differences in the Response of Rabbit Small Intestine to Heat–Labile and Heat–Stable Enterotoxins of *Escherichia Coli*", *Infection and Immunity*, 1973, 7, 873–880.

Fischman et al., "A Ticket to Ride: Peptide Radiopharmaceuticals", *J. Nucl. Med.*, 1993, 34, 2253–2263.

Fitzgerald et al., "Adenovirus–Induced Release of Epidermal Growth Factor and Pseudomonas Toxin into the Cytosol of KB Cells during Receptor–Mediated Endocytosis", *Cell*, 1983, 32, 607–617.

Fitzgerald, "Construction of Immunotoxins Using Pseudomonas Exotoxin A", *Methods in Enzymology*, 1987, 151, 139–145.

(List continued on next page.)

*Primary Examiner*—Scott W. Houtteman
*Attorney, Agent, or Firm*—Woodcock Washburn Kurtz Mackiewicz & Norris LLP

[57] ABSTRACT

Conjugated compounds that comprise an ST receptor binding moiety and an active moiety that is an antisense molecule are disclosed. Pharmaceutical compositions which comprise conjugated compounds that comprise an ST receptor binding moiety and an active moiety that is an antisense molecule are disclosed including pharmaceutical compositions that have enteric formulations. Methods of treating an individual suspected of suffering from colorectal cancer and methods of preventing colorectal cancer are disclosed.

19 Claims, No Drawings

OTHER PUBLICATIONS

Franz et al., "The Production of $^{99m}$Tc–Labeled Conjugated Antibodies Using A Cyclam–Based Bifunctional Chelating Agent", *J. Nucl. Med. Biol.*, 1987, 14, 569–572.

Giannella et al., "Development of a Radioimmunoassay for *Escherichia coli* Heat–Stable Enterotoxin: Comparison with the Suckling Mouse Bioassay", *Infection and Immunity*, 1981, 33, 186–192.

Gros, O., "Biochemical Aspects of Immunotoxin Preparation", *J. Immunol. Meth.*, 1985, 81, 283–297.

Guarino, A. et al., "$T^{84}$ Cell Receptor Binding and Guanyl Cyclas Activaiton by *Escherichia coli* Heat–Stable Toxin", *Am. J. Physiol.*, 1987, 253 (Gastrointest. Liver Physiol. 16): G775–780.

Gyles, C.L., "Discussion: Heat–Labile and Heat–Stable Forms of the Enterotoxin from *E. Coli* Strains Enteropathogenic For Pigs", *Ann N.Y. Acad. Sci.*, 1979, 16, 314–321.

Hakki et al., "Solubilization and Characterization of Functionally Coupled *Escherichia Coli* Heat–Stable Toxin Recpeptors and Particulate Guanylate Cyclase Associated with the Cytoskeleton Compartment of Intestinal Membranes", *Int. J. Biochem*, 1993, 25, 557–566.

Hugues et al., "Identification and Characterization of a New Family of High–Affinity Receptors for *Escherichia Coli* Heat–Stable Enterotoxin in Rat Intestinal Membranes", *Biochem.*, 1991, 30, 10738–10745.

Humm et al., "Dosimetric Aspects of Radiolabeled Antibodies for Tumor Therapy", *J. Nucl. Med.*, 1986, 27, 1490–1497.

Klipstein et al., "Development of a Vaccine of Cross–Linked Heat–Stable and Heat–Labile Enterotoxins that Protects Against *Escherichia Coli* Producing Either Enterotoxin", *Infection and Immunity*, 1982, 37, 550–557.

Krejcarek and Tucker, "Covalent Attachment of Chelating Groups to Macromolecules", *Biochem. Biophys. Res. Commun.*, 1977, 77, 581–585.

Kwok, "Calculation of Radiation Doses for Nonuniformly Distributed $\beta$ and $\gamma$ Radionuclides in Soft Tissue", *Med. Phys.*, 1985, 12, 405–412.

Leonard et al., "Kinetics of Protein Synthesis Inactivation in Human T–Lymphocytes by Selective Monoclonal Antibody–Ricin Conjugates", *Cancer Res.*, 1985, 45, 5263–5269.

Magerstadt, M., *Antibody Conjugates and Malignant Disease*Boca Raton: CRC Press, 110–152 (1991).

Masuho et al., "Importance of the Antigen–Binding Valency and the Nature of the Cross–Linking Bond in Ricin A–Chain Conjugates with Antibody", *J. Biochem.*, 1982, 91, 1583–1591.

Merrifield, "Solid Phase Peptide Synthesis. I. The Synthesis of a Tetrapeptide", *J. Am. Chem. Society*, 1963, 15, 2149–2154.

Michel and Dirkx, "Fluorescence Studies of Nucleotides Binding to Diphtheria Toxin and Its Fragment A", *Biochimica et Biophysia Acta*, 1974, 365, 15–27.

Moseley et al., "Isolation and Nucleotide Sequence Determination of a Gene Encoding a Heat–Stable Enterotoxin of *Escherichia Coli*", *Infection and Immunity*, 1983, 39, 1167–1174.

Okamoto et al., "Substitutions of Cysteine Residues of *Escherichia Coli* Heat–Stable Enterotoxin By Oligonucleotide–Directed Mutagenesis", *Infection and Immunity*, 1987, 55, 2121–2125.

Richardson et al., "Astatine ($^{211}$At) as a Therapeutic Radionuclide. The Plasma: Blood Cell distribution in Vitro", *Nucl. Med. Biol.*, 1986, 13, 583–584.

Sack, "Human Diarrheal Disease Caused by Enterotoxigenic *Escherichia Coli*", *Ann. Rev. Microbiol.*, 1975, 29, 333–353.

Shimonishi et al., "Mode of Disulfide Bond Formation of a Heat–Stable Enterotoxin ($ST_h$) Produced by a Human Strain of Enterotoxigenic *Escherichia Coli*", *FEBS Letters*, 1987, 215, 165–170.

So and McCarthy, "Nucleotide Sequence of the Bacterial Transposon Tn1681 Encoding a Heat–Stable (ST) Toxin and Its Identification in Enterotoxigenic *Escherichia Coli* Strains", *Proc. Natl. Acad. Sci. USA*, 1980, 77, 4011–4015.

Spitler et al., "Therapy of Patients with Malignant Melanoma Using a Monoclonal Antimelanoma Antibody–Ricin A Chain Immunotoxin", *Cancer Res.*, 1987, 47, 1717–1723.

Steinsträβer et al., "Selection of Nuclides for Immunoscintigraphy/Immunotherapy", *J. Nucl. Med.*, 1988, 5, 875.

Thompson, "*Escherichia coli* Heat–Stable Enterotoxins and their Receptors", *Pathol. Immunopathol. Res.*, 1987, 6, 103–116.

Thompson et al, "Biological and Immunological Characteristics of $^{125}$I–4Tyr and –18Tyr *Escherichia coli* Heat–Stable Enterotoxin Species Purified by High–Performance Liquid Chromatography", *Analytical Biochem.*, 1985, 148, 26–36.

Thorpe et al., "New Coupling Agents for the Synthesis of Immunotoxins Containing a Hindered Disulfide Bond with Improved Stability In Vivo", *Cancer Res.*, 1987, 47, 5924–5931.

Vaandrager, A. et al, "Atriopeptins and *Escherichia coli* Enterotoxin $ST^a$ Have Different Sites of Aciton in Mammalian Intestine", *Gastroenterology*, 1992, 102(4), 1161–1169.

Waldman et al., "Influence of a Glycine or Proline Substitution on the Functional Properties of a 14–Amino–Acid Analog of *Escherichia Coli* Heat–Stable Enterotoxin", *Infection and Immunity*, 1989, 57, 2420–2424.

Wessels and Rogus, "Radionuclide Selection and Model Absorbed Dose Calculations for Radiolabeled Tumor Associated Antibodies", *Med. Phys.*, 1984, 11, 638–645.

Worrell et al., "Effect of Linkage Variation on Pharmacokinetics of Ricin A Chain–Antibody Conjugates in Normal Rats", *Anti–Cancer Drug Design*, 1986, 1, 179–188.

Yoshimura et al, "Essential Structure for Full Enterotoxigenic Activity of Heat–Stable Enterotoxin Produced by Enterotoxigenic *Escherichia Coli*", *FEBS 2232*, 1985, vol. 181, 138–142.

Alexander, R.J. et al., "Oncogene Alterations in Rat Colon tumors Induced by—methyl–N–nitrosourea", *Am. J. Med. Sci.*, 1992, 303(1), 16–24.

Bold, R.J. et al., "Experimental Gene Therapy of Human Colon Cancer", *Surgery*, 1994, 116(2), 189–196.

Carrithers et al., "*Escherichia coli* Heat–Stable Toxin Receptors in Human Colonic Tumors", *Gastroenterology*, 1994, 107, 1653–1661.

Carrithers et al., "Guanylyl cyclase C is a selective marker for metastatic colorectal tumors in human extraintestinal tissues", *Proc. Natl. Acad. Sci. USA*, 1996, 93, 14827–14832.

Ciardiello, F. et al., "Inhibition of CRIPTO Expression and Tumorigenicity in Human Colon Cancer Cells by Antisense RNA and Oligodeoxynucleotides", *Oncogene*, 1994, 9(1), 291–298.

Collins, J.F. et al., "C–myc Antisense Oligonucleotides Inhibit the Colony–forming Capacity of Colo 320 Colonic Carcinoma Cells", *J. Clin. Investigation,* 1992, 89(5), 1523–1527.

Cooney, M. et al., "Site–Specific Oligonucleotide Binding Represses Transcription of the Human c–myc Gene in Vitro", *Science,* 1988, 241, 456–459.

Dayhoff, M.D., "Atlas of Protein Sequence and Structure", *Nat. Biomed. Res. Found.,* 1978, vol. 5, Supp. 3, Washington, D.C.

Helene, C. and Toulme, "Specific Regulation of Gene Expression by Antisense, Sense and Antigene Nucleic Acids", *Biochem. Biophys. Acta,* 1990, 1049, 99–125.

Hugues et al., "Affinity Purification of Functional Receptors for *Escherichia coli* Heat–Stable Enterotoxin from Rat Intestine", *Biochem.,* 1992, 31(1), 12–16.

Kent, S. and Clark–Lewis in "Synthetic Peptides in Biology and Medicine", Alitalo, K. et al. (eds.), Science Publishers, Amsterdam, 1985, pp. 29–57.

Knyazev, P.G. et al., "Complex Characteristics of the Alterations of Oncogenes HER–2/ERBB–2, HER–1/ERBB–1, HRAS–1, C–MYC and Anti–Oncogenes p53, RB1, as well as Deletions of Loci of Chromosome 17 in Colon Carcinoma", *Molekuliarnaia Biologiia,* 1992, 26(5), 1134–1147 (English translation).

Melani, C. et al., "Inhibition of Proliferation by c–myb Antisense Oligodeoxynucleotides in Colon Adenocarcinoma Cell Lines that Express c–myb", *Cancer Res.,* 1991, 51(1), 2897–2901.

Nielsen, P.E. et al., "Sequence–specific Transcription Arrest by Peptide Nucleic Acid Bound to the DNA Template Strand", *Gene,* 1994, 149, 139–145.

Orkin et al., "Report and Recommendations of the Panel to Assess the NIH Investment in Research on Gene Therapy", p. 41, Dec., 1995.

Ramsay, R.G. et al., "Myb Expression is Higher in Malignant Human Colonic Carcinoma and Premalignant Adenomatous Polyps than in Normal Mucosa", *Cell Growth & Differentiantion,* 1992, 3(10), 723–30.

Rodriguez–Alfageme, C. et al., "Suppression of Deregulated c–MYC Expression in Human Colon Carcinoma Cells by Chromosome 5 Transfer", *PNAS USA,* 1992, 89(4), 1482–1486.

Sizeland, A.M. et al., "Antisense Transforming Growth Factor Alpha Oligonucleotides Inhibit Autocrine Stimulated Proliferation of a Colon Carcinoma Cell Line", *Mol. Biol. Cell,* 1992, 3(11), 1235–1243.

Tanaka, K. et al., "Suppression of Tumorigenicity in Human Colon Carcinoma Cells by Introduction of Normal Chromosome 1p36 Region", *Oncogene,* 1993, 8(8), 2253–2258.

Takekawa, M. et al., "Chromosomal Localization fo the Protein Tyrosine Phosphatase G1 Gene and Characterization of the Aberrant Transcripts in Human Colon Cancer Cells", *FEBS Letters,* 1994, 339(3), 222–228.

Toribara, N.W. and Sleisenger, "Screening for Colorectal Cancer", *New England J. Med.,* 1995, 332, 861–867.

Urbanski et al., "Internalization of *E. coli* ST mediated by guanylyl cyclase C in T84 human colon carcinoma cells", *Biochim. Et Biophys. Acta,* 1995, 1245, 29–36.

Yokozaki, H. et al., "An Antisense Oligodeoxynucleotide that Depletes RI Alpha Subunit of Cyclic AMP–dependent Protein Kinase Induces Growth Inhibition in Human Cancer Cells", Cancer Research, 1993, 53(4), 868–872.

```
                            SEQUENCE LISTING (1) GENERAL INFORMATION:

(iii) NUMBER OF SEQUENCES: 54

(2) INFORMATION FOR SEQ ID NO:1:

(i) SEQUENCE CHARACTERISTICS:
              (A) LENGTH: 57 base pairs
              (B) TYPE: nucleic acid
              (C) STRANDEDNESS: double
              (D) TOPOLOGY: both (ii) MOLECULE TYPE: cDNA (ix) FEATURE:
              (A) NAME/KEY: CDS
              (B) LOCATION: 1..57

(xi) SEQUENCE DESCRIPTION: SEQ ID NO:1:

AAC AAC ACA TTT TAC TGC TGT GAA CTT TGT TGT AAT CCT GCC TGT GCT        48
    Asn Asn Thr Phe Tyr Cys Cys Glu Leu Cys Cys Asn Pro Ala Cys Ala
     1               5                  10                  15

GGA TGT TAT                                                            57
    Gly Cys Tyr (2) INFORMATION FOR SEQ ID NO:2:

(i) SEQUENCE CHARACTERISTICS:
              (A) LENGTH: 19 amino acids
              (B) TYPE: amino acid
              (D) TOPOLOGY: linear (ii) MOLECULE TYPE: protein (xi) SEQUENCE DESCRIPTION: SEQ ID NO:2:

Asn Asn Thr Phe Tyr Cys Cys Glu Leu Cys Cys Asn Pro Ala Cys Ala
     1               5                  10                  15

Gly Cys Tyr (2) INFORMATION FOR SEQ ID NO:3:

(i) SEQUENCE CHARACTERISTICS:
              (A) LENGTH: 18 amino acids
              (B) TYPE: amino acid
```

(D) TOPOLOGY: linear (ii) MOLECULE TYPE: peptide (xi) SEQUENCE DESCRIPTION: SEQ ID NO:3:

Asn Thr Phe Tyr Cys Cys Glu Leu Cys Cys Tyr Pro Ala Cys Ala Gly
1               5                   10                  15

Cys Asn (2) INFORMATION FOR SEQ ID NO:4:

(i) SEQUENCE CHARACTERISTICS:
        (A) LENGTH: 57 base pairs
        (B) TYPE: nucleic acid
        (C) STRANDEDNESS: double
        (D) TOPOLOGY: both (ii) MOLECULE TYPE: cDNA (ix) FEATURE:
        (A) NAME/KEY: CDS
        (B) LOCATION: 1..57

(xi) SEQUENCE DESCRIPTION: SEQ ID NO:4:

AAT AGT AGC AAT TAC TGC TGT GAA TTG TGT TGT AAT CCT GCT TGT AAC        48
Asn Ser Ser Asn Tyr Cys Cys Glu Leu Cys Cys Asn Pro Ala Cys Asn
1               5                   10                  15

GGG TGC TAT                                                            57
Gly Cys Tyr (2) INFORMATION FOR SEQ ID NO:5:

(i) SEQUENCE CHARACTERISTICS:
        (A) LENGTH: 19 amino acids
        (B) TYPE: amino acid
        (D) TOPOLOGY: linear (ii) MOLECULE TYPE: protein (xi) SEQUENCE DESCRIPTION: SEQ ID NO:5:

Asn Ser Ser Asn Tyr Cys Cys Glu Leu Cys Cys Asn Pro Ala Cys Asn
1               5                   10                  15

Gly Cys Tyr (2) INFORMATION FOR SEQ ID NO:6:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (xi) SEQUENCE DESCRIPTION: SEQ ID NO:6:

Pro Asn Thr Cys Glu Ile Cys Ala Tyr Ala Ala Cys Thr Gly Cys
1               5                   10                  15

(2) INFORMATION FOR SEQ ID NO:7:

(i) SEQUENCE CHARACTERISTICS:
        (A) LENGTH: 18 amino acids
        (B) TYPE: amino acid
        (D) TOPOLOGY: linear (ii) MOLECULE TYPE: peptide (xi) SEQUENCE DESCRIPTION: SEQ ID NO:7:

```
Asn Asn Thr Phe Tyr Cys Cys Glu Leu Cys Cys Asn Pro Ala Cys Ala
 1               5                  10                  15
Gly Cys
```

(2) INFORMATION FOR SEQ ID NO:8:

(i) SEQUENCE CHARACTERISTICS:
        (A) LENGTH: 17 amino acids
        (B) TYPE: amino acid
        (D) TOPOLOGY: linear (ii) MOLECULE TYPE: peptide (xi) SEQUENCE DESCRIPTION: SEQ ID NO:8:

```
Asn Thr Phe Tyr Cys Cys Glu Leu Cys Cys Asn Pro Ala Cys Ala Gly
 1               5                  10                  15
Cys
```

(2) INFORMATION FOR SEQ ID NO:9:

(i) SEQUENCE CHARACTERISTICS:
        (A) LENGTH: 16 amino acids
        (B) TYPE: amino acid
        (D) TOPOLOGY: linear (ii) MOLECULE TYPE: peptide (xi) SEQUENCE DESCRIPTION: SEQ ID NO:9:

```
Thr Phe Tyr Cys Cys Glu Leu Cys Cys Asn Pro Ala Cys Ala Gly Cys
 1               5                  10                  15
```

(2) INFORMATION FOR SEQ ID NO:10:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (xi) SEQUENCE DESCRIPTION: SEQ ID NO:10:

```
Phe Tyr Cys Cys Glu Leu Cys Cys Asn Pro Ala Cys Ala Gly Cys
 1               5                  10                  15
```

(2) INFORMATION FOR SEQ ID NO:11:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (xi) SEQUENCE DESCRIPTION: SEQ ID NO:11:

```
Tyr Cys Cys Glu Leu Cys Cys Asn Pro Ala Cys Ala Gly Cys
 1               5                  10
```

(2) INFORMATION FOR SEQ ID NO:12:

(i) SEQUENCE CHARACTERISTICS:
        (A) LENGTH: 13 amino acids
        (B) TYPE: amino acid
        (D) TOPOLOGY: linear (ii) MOLECULE TYPE: peptide (xi) SEQUENCE DESCRIPTION: SEQ ID NO:12:

```
Cys Cys Glu Leu Cys Cys Asn Pro Ala Cys Ala Gly Cys
  1               5                  10
```

(2) INFORMATION FOR SEQ ID NO:13:

(i) SEQUENCE CHARACTERISTICS:
        (A) LENGTH: 18 amino acids
        (B) TYPE: amino acid
        (D) TOPOLOGY: linear (ii) MOLECULE TYPE: peptide (xi) SEQUENCE DESCRIPTION: SEQ ID NO:13:

```
Asn Thr Phe Tyr Cys Cys Glu Leu Cys Cys Asn Pro Ala Cys Ala Gly
  1               5                  10                  15
Cys Tyr
```

(2) INFORMATION FOR SEQ ID NO:14:

(i) SEQUENCE CHARACTERISTICS:
        (A) LENGTH: 17 amino acids
        (B) TYPE: amino acid
        (D) TOPOLOGY: linear (ii) MOLECULE TYPE: peptide (xi) SEQUENCE DESCRIPTION: SEQ ID NO:14:

```
Thr Phe Tyr Cys Cys Glu Leu Cys Cys Asn Pro Ala Cys Ala Gly Cys
  1               5                  10                  15
Tyr
```

(2) INFORMATION FOR SEQ ID NO:15:

(i) SEQUENCE CHARACTERISTICS:
        (A) LENGTH: 16 amino acids
        (B) TYPE: amino acid
        (D) TOPOLOGY: linear (ii) MOLECULE TYPE: peptide (xi) SEQUENCE DESCRIPTION: SEQ ID NO:15:

```
Phe Tyr Cys Cys Glu Leu Cys Cys Asn Pro Ala Cys Ala Gly Cys Tyr
  1               5                  10                  15
```

(2) INFORMATION FOR SEQ ID NO:16:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (xi) SEQUENCE DESCRIPTION: SEQ ID NO:16:

```
Tyr Cys Cys Glu Leu Cys Cys Asn Pro Ala Cys Ala Gly Cys Tyr
  1               5                  10                  15
```

(2) INFORMATION FOR SEQ ID NO:17:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (xi) SEQUENCE DESCRIPTION: SEQ ID NO:17:

```
Cys Cys Glu Leu Cys Cys Asn Pro Ala Cys Ala Gly Cys Tyr
 1               5                  10
```

(2) INFORMATION FOR SEQ ID NO:18:

(i) SEQUENCE CHARACTERISTICS:
        (A) LENGTH: 17 amino acids
        (B) TYPE: amino acid
        (D) TOPOLOGY: linear (ii) MOLECULE TYPE: peptide (xi) SEQUENCE DESCRIPTION: SEQ ID NO:18:

```
Asn Thr Phe Tyr Cys Cys Glu Leu Cys Cys Tyr Pro Ala Cys Ala Gly
 1               5                  10                  15
Cys
```

(2) INFORMATION FOR SEQ ID NO:19:

(i) SEQUENCE CHARACTERISTICS:
        (A) LENGTH: 16 amino acids
        (B) TYPE: amino acid
        (D) TOPOLOGY: linear (ii) MOLECULE TYPE: peptide (xi) SEQUENCE DESCRIPTION: SEQ ID NO:19:

```
Thr Phe Tyr Cys Cys Glu Leu Cys Cys Tyr Pro Ala Cys Ala Gly Cys
 1               5                  10                  15
```

(2) INFORMATION FOR SEQ ID NO:20:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (xi) SEQUENCE DESCRIPTION: SEQ ID NO:20:

```
Phe Tyr Cys Cys Glu Leu Cys Cys Tyr Pro Ala Cys Ala Gly Cys
 1               5                  10                  15
```

(2) INFORMATION FOR SEQ ID NO:21:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (xi) SEQUENCE DESCRIPTION: SEQ ID NO:21:

```
Tyr Cys Cys Glu Leu Cys Cys Tyr Pro Ala Cys Ala Gly Cys
 1               5                  10
```

(2) INFORMATION FOR SEQ ID NO:22:

(i) SEQUENCE CHARACTERISTICS:
        (A) LENGTH: 13 amino acids
        (B) TYPE: amino acid
        (D) TOPOLOGY: linear (ii) MOLECULE TYPE: peptide (xi) SEQUENCE DESCRIPTION: SEQ ID NO:22:

```
Cys Cys Glu Leu Cys Cys Tyr Pro Ala Cys Ala Gly Cys
 1               5                  10
```

(2) INFORMATION FOR SEQ ID NO:23:

(i) SEQUENCE CHARACTERISTICS:
        (A) LENGTH: 17 amino acids
        (B) TYPE: amino acid
        (D) TOPOLOGY: linear (ii) MOLECULE TYPE: peptide (xi) SEQUENCE DESCRIPTION: SEQ ID NO:23:

```
Thr Phe Tyr Cys Cys Glu Leu Cys Cys Tyr Pro Ala Cys Ala Gly Cys
  1               5                  10                  15
Asn
```

(2) INFORMATION FOR SEQ ID NO:24:

(i) SEQUENCE CHARACTERISTICS:
        (A) LENGTH: 16 amino acids
        (B) TYPE: amino acid
        (D) TOPOLOGY: linear (ii) MOLECULE TYPE: peptide (xi) SEQUENCE DESCRIPTION: SEQ ID NO:24:

```
Phe Tyr Cys Cys Glu Leu Cys Cys Tyr Pro Ala Cys Ala Gly Cys Asn
  1               5                  10                  15
```

(2) INFORMATION FOR SEQ ID NO:25:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (xi) SEQUENCE DESCRIPTION: SEQ ID NO:25:

```
Tyr Cys Cys Glu Leu Cys Cys Tyr Pro Ala Cys Ala Gly Cys Asn
  1               5                  10                  15
```

(2) INFORMATION FOR SEQ ID NO:26:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (xi) SEQUENCE DESCRIPTION: SEQ ID NO:26:

```
Cys Cys Glu Leu Cys Cys Tyr Pro Ala Cys Ala Gly Cys Asn
  1               5                  10
```

(2) INFORMATION FOR SEQ ID NO:27:

(i) SEQUENCE CHARACTERISTICS:
        (A) LENGTH: 18 amino acids
        (B) TYPE: amino acid
        (D) TOPOLOGY: linear (ii) MOLECULE TYPE: peptide (xi) SEQUENCE DESCRIPTION: SEQ ID NO:27:

```
Asn Ser Ser Asn Tyr Cys Cys Glu Leu Cys Cys Asn Pro Ala Cys Thr
  1               5                  10                  15
Gly Cys
```

(2) INFORMATION FOR SEQ ID NO:28:

(i) SEQUENCE CHARACTERISTICS:
        (A) LENGTH: 17 amino acids
        (B) TYPE: amino acid
        (D) TOPOLOGY: linear (ii) MOLECULE TYPE: peptide (xi) SEQUENCE DESCRIPTION: SEQ ID NO:28:

Ser Ser Asn Tyr Cys Cys Glu Leu Cys Cys Asn Pro Ala Cys Thr Gly
  1               5                  10                  15
Cys (2) INFORMATION FOR SEQ ID NO:29:

(i) SEQUENCE CHARACTERISTICS:
        (A) LENGTH: 16 amino acids
        (B) TYPE: amino acid
        (D) TOPOLOGY: linear (ii) MOLECULE TYPE: peptide (xi) SEQUENCE DESCRIPTION: SEQ ID NO:29:

Ser Asn Tyr Cys Cys Glu Leu Cys Cys Asn Pro Ala Cys Thr Gly Cys
  1               5                  10                  15

(2) INFORMATION FOR SEQ ID NO:30:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (xi) SEQUENCE DESCRIPTION: SEQ ID NO:30:

Asn Tyr Cys Cys Glu Leu Cys Cys Asn Pro Ala Cys Thr Gly Cys
  1               5                  10                  15

(2) INFORMATION FOR SEQ ID NO:31:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (xi) SEQUENCE DESCRIPTION: SEQ ID NO:31:

Tyr Cys Cys Glu Leu Cys Cys Asn Pro Ala Cys Thr Gly Cys
  1               5                  10

(2) INFORMATION FOR SEQ ID NO:32:

(i) SEQUENCE CHARACTERISTICS:
        (A) LENGTH: 13 amino acids
        (B) TYPE: amino acid
        (D) TOPOLOGY: linear (ii) MOLECULE TYPE: peptide (xi) SEQUENCE DESCRIPTION: SEQ ID NO:32:

Cys Cys Glu Leu Cys Cys Asn Pro Ala Cys Thr Gly Cys
  1               5                  10

(2) INFORMATION FOR SEQ ID NO:33:

(i) SEQUENCE CHARACTERISTICS:
        (A) LENGTH: 18 amino acids
        (B) TYPE: amino acid
        (D) TOPOLOGY: linear (ii) MOLECULE TYPE: peptide (xi) SEQUENCE DESCRIPTION: SEQ ID NO:33:

Ser Ser Asn Tyr Cys Cys Glu Leu Cys Cys Asn Pro Ala Cys Thr Gly
1               5                   10                  15

Cys Tyr (2) INFORMATION FOR SEQ ID NO:34:

(i) SEQUENCE CHARACTERISTICS:
        (A) LENGTH: 17 amino acids
        (B) TYPE: amino acid
        (D) TOPOLOGY: linear (ii) MOLECULE TYPE: peptide (xi) SEQUENCE DESCRIPTION: SEQ ID NO:34:

Ser Asn Tyr Cys Cys Glu Leu Cys Cys Asn Pro Ala Cys Thr Gly Cys
1               5                   10                  15

Tyr (2) INFORMATION FOR SEQ ID NO:35:

(i) SEQUENCE CHARACTERISTICS:
        (A) LENGTH: 16 amino acids
        (B) TYPE: amino acid
        (D) TOPOLOGY: linear (ii) MOLECULE TYPE: peptide (xi) SEQUENCE DESCRIPTION: SEQ ID NO:35:

Asn Tyr Cys Cys Glu Leu Cys Cys Asn Pro Ala Cys Thr Gly Cys Tyr
1               5                   10                  15

(2) INFORMATION FOR SEQ ID NO:36:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (xi) SEQUENCE DESCRIPTION: SEQ ID NO:36:

Tyr Cys Cys Glu Leu Cys Cys Asn Pro Ala Cys Thr Gly Cys Tyr
1               5                   10                  15

(2) INFORMATION FOR SEQ ID NO:37:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (xi) SEQUENCE DESCRIPTION: SEQ ID NO:37:

Cys Cys Glu Leu Cys Cys Asn Pro Ala Cys Thr Gly Cys Tyr
1               5                   10

(2) INFORMATION FOR SEQ ID NO:38:

(i) SEQUENCE CHARACTERISTICS:
        (A) LENGTH: 18 amino acids
        (B) TYPE: amino acid
        (D) TOPOLOGY: linear (ii) MOLECULE TYPE: peptide (xi) SEQUENCE DESCRIPTION: SEQ ID NO:38:

Asn Thr Phe Tyr Cys Cys Glu Leu Cys Cys Asn Pro Ala Cys Ala Gly
 1               5                  10                  15

Cys Tyr (2) INFORMATION FOR SEQ ID NO:39:

(i) SEQUENCE CHARACTERISTICS:
        (A) LENGTH: 18 amino acids
        (B) TYPE: amino acid
        (D) TOPOLOGY: linear (ii) MOLECULE TYPE: peptide (xi) SEQUENCE DESCRIPTION: SEQ ID NO:39:

Asn Thr Phe Tyr Cys Cys Glu Leu Cys Cys Ala Pro Ala Cys Ala Gly
 1               5                  10                  15

Cys Tyr (2) INFORMATION FOR SEQ ID NO:40:

(i) SEQUENCE CHARACTERISTICS:
        (A) LENGTH: 18 amino acids
        (B) TYPE: amino acid
        (D) TOPOLOGY: linear (ii) MOLECULE TYPE: peptide (xi) SEQUENCE DESCRIPTION: SEQ ID NO:40:

Asn Thr Phe Tyr Cys Cys Glu Leu Cys Cys Asn Ala Ala Cys Ala Gly
 1               5                  10                  15

Cys Tyr (2) INFORMATION FOR SEQ ID NO:41:

(i) SEQUENCE CHARACTERISTICS:
        (A) LENGTH: 17 amino acids
        (B) TYPE: amino acid
        (D) TOPOLOGY: linear (ii) MOLECULE TYPE: peptide (xi) SEQUENCE DESCRIPTION: SEQ ID NO:41:

Asn Thr Phe Tyr Cys Cys Glu Leu Cys Cys Asn Pro Ala Cys Ala Gly
 1               5                  10                  15

Cys (2) INFORMATION FOR SEQ ID NO:42:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (xi) SEQUENCE DESCRIPTION: SEQ ID NO:42:

-continued

```
Tyr Cys Cys Glu Leu Cys Cys Asn Pro Ala Cys Ala Gly Cys Tyr
 1               5                  10                  15
```

(2) INFORMATION FOR SEQ ID NO:43:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (xi) SEQUENCE DESCRIPTION: SEQ ID NO:43:

```
Tyr Cys Cys Glu Leu Cys Cys Asn Pro Ala Cys Ala Gly Cys
 1               5                  10
```

(2) INFORMATION FOR SEQ ID NO:44:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (xi) SEQUENCE DESCRIPTION: SEQ ID NO:44:

```
Cys Cys Glu Leu Cys Cys Asn Pro Ala Cys Ala Gly Cys Tyr
 1               5                  10
```

(2) INFORMATION FOR SEQ ID NO:45:

(i) SEQUENCE CHARACTERISTICS:
        (A) LENGTH: 13 amino acids
        (B) TYPE: amino acid
        (D) TOPOLOGY: linear (ii) MOLECULE TYPE: peptide (xi) SEQUENCE DESCRIPTION: SEQ ID NO:45:

```
Cys Cys Glu Leu Cys Cys Asn Pro Ala Cys Ala Gly Cys
 1               5                  10
```

(2) INFORMATION FOR SEQ ID NO:46:

(i) SEQUENCE CHARACTERISTICS:
        (A) LENGTH: 25 amino acids
        (B) TYPE: amino acid
        (D) TOPOLOGY: linear (ii) MOLECULE TYPE: peptide (xi) SEQUENCE DESCRIPTION: SEQ ID NO:46:

```
Gln Ala Cys Asp Pro Pro Ser Pro Pro Ala Glu Val Cys Cys Asp Val
 1               5                  10                  15

Cys Cys Asn Pro Ala Cys Ala Gly Cys
                20                  25
```

(2) INFORMATION FOR SEQ ID NO:47:

(i) SEQUENCE CHARACTERISTICS:
        (A) LENGTH: 16 amino acids
        (B) TYPE: amino acid
        (D) TOPOLOGY: linear (ii) MOLECULE TYPE: peptide (xi) SEQUENCE DESCRIPTION: SEQ ID NO:47:

```
Ile Asp Cys Cys Ile Cys Cys Asn Pro Ala Cys Phe Gly Cys Leu Asn
```

-continued

```
1               5              10              15
```

(2) INFORMATION FOR SEQ ID NO:48:

(i) SEQUENCE CHARACTERISTICS:
        (A) LENGTH: 18 amino acids
        (B) TYPE: amino acid
        (D) TOPOLOGY: linear (ii) MOLECULE TYPE: peptide (xi) SEQUENCE DESCRIPTION: SEQ ID NO:48:

```
Ser Ser Asp Trp Asp Cys Cys Asp Val Cys Cys Asn Pro Ala Cys Ala
1               5                  10                  15
Gly Cys
```

(2) INFORMATION FOR SEQ ID NO:49:

(i) SEQUENCE CHARACTERISTICS:
        (A) LENGTH: 19 amino acids
        (B) TYPE: amino acid
        (D) TOPOLOGY: linear (ii) MOLECULE TYPE: peptide (xi) SEQUENCE DESCRIPTION: SEQ ID NO:49:

```
Asn Ser Ser Asn Tyr Cys Cys Glu Leu Cys Cys Tyr Pro Ala Cys Thr
1               5                  10                  15
Gly Cys Tyr
```

(2) INFORMATION FOR SEQ ID NO:50:

(i) SEQUENCE CHARACTERISTICS:
        (A) LENGTH: 13 amino acids
        (B) TYPE: amino acid
        (D) TOPOLOGY: linear (ii) MOLECULE TYPE: peptide (xi) SEQUENCE DESCRIPTION: SEQ ID NO:50:

```
Cys Cys Asp Val Cys Cys Asn Pro Ala Cys Thr Gly Cys
1               5                  10
```

(2) INFORMATION FOR SEQ ID NO:51:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (xi) SEQUENCE DESCRIPTION: SEQ ID NO:51:

```
Cys Cys Asp Val Cys Cys Tyr Pro Ala Cys Thr Gly Cys Tyr
1               5                  10
```

(2) INFORMATION FOR SEQ ID NO:52:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (xi) SEQUENCE DESCRIPTION: SEQ ID NO:52:

```
Cys Cys Asp Leu Cys Cys Asn Pro Ala Cys Ala Gly Cys Tyr
```

-continued

```
                1               5                    10
```

(2) INFORMATION FOR SEQ ID NO:53:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (xi) SEQUENCE DESCRIPTION: SEQ ID NO:53:

```
Cys Cys Gln Leu Cys Cys Asn Pro Ala Cys Thr Gly Cys Tyr
 1               5                    10
```

(2) INFORMATION FOR SEQ ID NO:54:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (xi) SEQUENCE DESCRIPTION: SEQ ID NO:54:

```
Pro Gly Thr Cys Glu Ile Cys Ala Tyr Ala Ala Cys Thr Gly Cys
 1               5                    10                  15
```

COMPOSITIONS THAT SPECIFICALLY BIND TO COLORECTAL CANCER CELLS AND METHODS OF USING THE SAME

CROSS REFERENCE TO RELATED PATENT APPLICATIONS

This Application is a continuation application of U.S. Ser. No. 08/467,920 filed Jun. 6, 1995, issued Oct. 5, 1999 as U.S. Pat. No. 5,962,220, which is a continuation in part application of U.S. Ser. No. 08/141,892 filed Oct. 26, 1993, issued May 21, 1996 as U.S. Pat. No. 5,518,888, which is herein incorporated by reference. This application is also related to U.S. Ser. No. 08/305,056 filed Sep. 13, 1994, issued Feb. 11, 1997 as U.S. Pat. No. 5,601,990, and PCT application Ser. No. PCT/US94/12232 filed Oct. 26, 1994, the disclosure of both of which are herein incorporated by reference.

FIELD OF THE INVENTION

The present invention relates to conjugated compounds which comprise an St receptor ligand moiety conjugated to an active moiety which is an antisense molecule. ST receptor binding moieties bind to the ST receptor which is found on human colon cells. The invention relates to antisense compositions specifically targeted to colon cells. The invention relates to methods of treating and preventing colorectal tumors.

BACKGROUND OF THE INVENTION

Colorectal cancer is the third most common neoplasm worldwide. The mortality rate of newly diagnosed large bowel cancer approaches 50% and there has been little improvement over the past 40 years. Most of this mortality reflects local, regional and distant metastases.

Surgery is the mainstay of treatment for colorectal cancer but recurrence is frequent. Colorectal cancer has proven resistant to chemotherapy, although limited success has been achieved using a combination of 5-fluorouracil and levamisole. Surgery has had the largest impact on survival and, in some patients with limited disease, achieves a cure. However, surgery removes bulk tumor, leaving behind microscopic residual disease which ultimately results in recrudescence.

Although current radiotherapeutic agents, chemotherapeutic agents and biological toxins are potent cytotoxins, they do not discriminate between normal and malignant cells, producing adverse effects and dose-limiting toxicities. Over the past decade, a novel approach has been employed to more specifically target agents to tumor cells, involving the conjugation of an active agent to molecules which binds preferentially to antigens that exist predominantly on tumor cells. These conjugates can be administered systemically and specifically bind to the targeted tumor cells. Theoretically, targeting permits uptake by cells of cytotoxic agents at concentrations which do not produce serious toxicities in normal tissues. Also, selective binding to targeted tumor cells facilitates detection of occult tumor and is therefore useful in designing imaging agents. Molecular targeting predominantly has employed monoclonal antibodies generated to antigens selectively expressed on tumor cells.

Monoclonal antibodies have also been employed to target specific therapeutic agents in colorectal cancer. Preclinical studies demonstrated that anti-CEA antibodies labelled with $^{90}$Yttrium inhibited human colon carcinoma xenografts in nude mice. Antibodies generated to colorectal cancer cells and coupled to mitomycin C or neocarzinostatin demonstrated an anti-tumor effect on human colon cancer xenografts in nude mice and 3 patients with colon cancer. Similar results in animals were obtained with monoclonal antibodies conjugated to ricin toxin A chain.

Due to the sensitivity, specificity, and adverseeffect profile of monoclonal antibodies, the results obtained using monoclonal antibody-based therapeutics have shown them to be less than ideal targeting tools. Although monoclonal antibodies have been generated to antigens selectively expressed on tumors, no truly cancer-specific antibody has been identified. Most antigens expressed on neoplastic cells appear to be quantitatively increased in these compared to normal cells but the antigens are nonetheless often present in normal cells. Thus, antibodies to such determinants can react with non-neoplastic tissues, resulting in significant toxicities. Also, antibodies are relatively large molecules and consequently, often evoke an immune response in patients. These immune responses can result in significant toxicities in patients upon re-exposure to the targeting agents and can prevent targeting by the monoclonal due to immune complex formation with degradation and excretion. Finally, binding of antibodies to tumor cells may be low and targeted agents may be delivered to cells in quantities insufficient to achieve detection or cytotoxicity.

There remains a need for compositions which can specifically target and prevent colorectal cancer. There is a need for therapeutic agents which can specifically bind to colorectal cells. There is a need for therapeutic agents which do not have toxic effects on normal cells. There is a need for improved methods of delivering antisense compositions to cells. There is a need for methods of treating individuals who are suspected of suffering from colorectal cancer. There is a need for methods of preventing colorectal cancer in individuals, particularly those identified as being at an increased risk of developing colorectal cancer.

SUMMARY OF THE INVENTION

The present invention relates to conjugated compounds which comprises an ST receptor binding moiety and a active moiety which comprises an antisense molecule.

The present invention relates to a pharmaceutical composition comprising a pharmaceutically acceptable carrier or diluent, and a conjugated compound which comprises an ST receptor binding moiety and an active moiety which comprises an antisense molecule.

The present invention relates to a method of treating an individual suspected of suffering from colorectal cancer comprising the steps of administering to a such an individual, a pharmaceutical composition comprising a pharmaceutically acceptable carrier or diluent and a therapeutically effective amount of a conjugated compound which comprises an ST receptor binding moiety and an active moiety which comprises an antisense molecule.

The present invention relates to a method of preventing colorectal cancer in an individual comprising the steps of administering to said individual a pharmaceutical composition comprising a pharmaceutically acceptable carrier or diluent and a prophylactically effective amount of a conjugated compound which comprises an ST receptor binding moiety and an active moiety which comprises an antisense molecule.

DESCRIPTION OF PREFERRED EMBODIMENTS OF THE INVENTION

As used herein, the terms "ST" and "native ST" are used interchangeably and are meant to refer to heat-stable toxin (ST) which is a peptide produced by *E. coli*, as well as other organisms. STs are naturally occurring peptides which 1) are naturally produced by organisms, 2) bind to the ST receptor and 3) activate the signal cascade that mediates ST-induced diarrhea.

As used herein, the term "ST receptor" is meant to refer to the receptors found on colorectal cells, including local and metastasized colorectal cancer cells, which bind to ST. In normal human individuals, ST receptors are found exclusively in cells of intestine, in particular in cells in the duodenum, small intestine (jejunum and ileum), the large intestine, colon (cecum, ascending colon, transverse colon, descending colon and sigmoid colon) and rectum.

As used herein, the term "ST receptor ligand" is meant to refer to compounds which specifically bind to the ST receptor. ST is an ST receptor ligand. An ST receptor ligand may be a peptide or a non-peptide.

As used herein, the term "ST receptor binding peptide" is meant to refer to ST receptor ligands that are peptides.

As used herein, the term "ST peptides" is meant to refer to ST receptor binding peptides selected from the group consisting of SEQ ID NO:2, SEQ ID NO:3, SEQ ID NOS:5–54 and fragments and derivatives thereof.

As used herein, the term "fragment" is meant to refer to peptide a) which has an amino acid sequence identical to a portion of an ST receptor binding peptide and b) which is capable of binding to the ST receptor.

As used herein, the term "derivative" is meant to refer to a peptide a) which has an amino acid sequence substantially identical to at least a portion of an ST receptor binding peptide and b) which is capable of binding to the ST receptor.

As used herein, the term "substantially identical" is meant to refer to an amino acid sequence that is the same as the amino acid sequence of an ST peptide except some of the resides are deleted or substituted with conservative amino acids or additional amino acids are inserted.

As used herein, the term "ST receptor binding moiety" is meant to refer to the portion of a conjugated compound that constitutes an ST receptor ligand.

As used herein, the term "active moiety" is meant to refer to the portion of a conjugated compound that constitutes the antisense composition.

As used herein, the term "antisense composition" and "antisense molecules" are used interchangeably and are meant to refer to compounds that regulate transcription or translation by hybridizing to DNA or RNA and inhibiting and/or preventing transcription or translation from taking place. Antisense molecules include nucleic acid molecules and derivatives and analogs thereof. Antisense molecules hybridize to DNA or RNA in the same manner as complementary nucleotide sequences do regardless of whether or not the antisense molecule is a nucleic acid molecule or a derivative or analog. Antisense molecules inhibit or prevent transcription or translation of genes whose expression is linked to colorectal cancer.

As used herein, the terms "conjugated compound" and "conjugated composition" are used interchangeably and meant to refer to a compound which comprises an ST receptor binding moiety and an active moiety. Conjugated compounds are capable of binding to the ST receptor on colon cells. Conjugated compounds according to the present invention comprise a portion which constitutes an ST receptor ligand and a portion which constitutes an antisense composition. Conjugated compositions may comprise crosslinkers and/or molecules that serve as spacers between the moieties.

As used herein, the terms "crosslinker", "crosslinking agent", "conjugating agent", "coupling agent", "condensation reagent" and "bifunctional crosslinker" are used interchangeably and are meant to refer to molecular groups which are used to attach the ST receptor ligand and the antisense molecule to thus form the conjugated compound.

As used herein, the term "colorectal cancer" is meant to include the well accepted medical definition that defines colorectal cancer as a medical condition characterized by cancer of cells of the intestinal tract below the small intestine (i.e. the large intestine (colon), including the cecum, ascending colon, transverse colon, descending colon, and sigmoid colon, and rectum). Additionally, as used herein, the term "colorectal cancer" is meant to further include medical conditions which are characterized by cancer of cells of the duodenum and small intestine (jejunum and ileum). The definition of colorectal cancer used herein is more expansive than the common medical definition but is provided as such since the cells of the duodenum and small intestine also contain ST receptors and are therefore amenable to the methods of the present invention using the compounds of the present invention.

As used herein, "an individual is suspected of being susceptible to colorectal cancer" is meant to refer to an individual who is at a particular risk of developing colorectal cancer. Examples of individuals at a particular risk of developing metastasized colorectal cancer are those whose family medical history indicates above average incidence of colorectal cancer among family members and/or those who have already developed colorectal cancer and have been effectively treated who therefore face a risk of relapse and recurrence.

As used herein, the terms "colorectal cancer-associated genes" and "cancer genes" are used interchangeably and are meant to refer to genes, such as oncogenes, whose expression or overexpression is associated with a transformed state of colorectal cells in colon cancer. Prevention or inhibition of cancer genes results in the prevention or reversal of the transformed phenotype.

ST, which is produced by *E. coli*, as well as other organisms, is responsible for endemic diarrhea in developing countries and travelers diarrhea. ST induces intestinal secretion by binding to specific receptors, ST receptors, in the apical brush border membranes of the mucosal cells lining the intestinal tract. Binding of ST to ST receptors is non-covalent and occurs in a concentration-dependent and saturable fashion. Once bound, ST—ST receptor complexes appear to be internalized by intestinal cells, i.e. transported from the surface into the interior of the cell. Binding of ST to ST receptors triggers a cascade of biochemical reactions in the apical membrane of these cells resulting in the production of a signal which induces intestinal cells to secrete fluids and electrolytes, resulting in diarrhea.

ST receptors are unique in that they are only localized in the apical brush border membranes of the cells lining the intestinal tract. Indeed, they are not found in any other cell type in placental mammals. In addition, ST receptors are almost exclusively localized to the apical membranes, with little being found in the basolateral membranes on the sides of intestinal cells.

Mucosal cells lining the intestine are joined together by tight junctions which form a barrier against the passage of intestinal contents into the blood stream and components of the blood stream into the intestinal lumen. Therefore, the apical location of ST receptors isolates these receptors from the circulatory system so that they may be considered to exist separate from the rest of the body; essentially the "outside" of the body. Therefore, the rest of the body is considered "outside" the intestinal tract. Compositions administered "outside" the intestinal tract are maintained apart and segregated from the only cells which normally express ST receptors. Conversely, tissue samples taken from tissue outside of the intestinal tract do not normally contain cells which express ST receptors.

In individuals suffering from colorectal cancer, the cancer cells are often derived from cells that produce and display the ST receptor and these cancer cells continue to produce and display the ST receptor on their cell surfaces. Indeed, T84 cells, which are human colonic adenocarcinoma cells isolated from lung metastases, express ST receptors on their cell surface. Similarly, HT29glu-cells, which are human colonic adenocarcinoma cells, express receptors for ST. Thus, in individuals suffering from colorectal cancer, some metastasized intestinal cancer cells express ST receptors.

An effort was undertaken to determine the proportion of colorectal tumors which have the ST receptor. Each of the tumors tested were independently confirmed to be colorectal cancer by standard techniques of surgical pathology. Every one of the colorectal cancer tumors tested, including local colorectal tumors and metastasized colorectal tumors (liver, lung, lymph node, peritoneum, ovary) possessed ST receptors. In each case, the affinity and density of receptors was amenable for targeting. Normal liver, lymphnode, peritoneum, gall bladder, ovary, stomach, kidney and lung cells were found not to possess ST receptors.

When such cancer cells metastasize, the metastasized cancer cells continue to produce and display the ST receptor. The expression of ST receptors on the surfaces of metastatic tumors provides a target for selective binding of conjugated compositions. ST receptors permit the absolutely specific targeting of therapeutic and diagnostic agents that are conjugated to ST receptor ligands to metastatic colorectal cancer cells.

The conjugated compositions of the present invention are useful for targeting cells that line the inner intestine wall including those cancer cells derived from such cells, including metastasized cancer cells as well as localized cancer and normal colon cells. The conjugated compositions will not bind to non-colorectal derived cells. Thus, the active moieties of conjugated compositions administered to an individual are delivered to cells which are derived from the intestinal tract such as local normal and cancerous colorectal cells and metastasized colorectal cells. Non-colorectal cells, lacking ST receptors, do not take up the conjugated compositions. Thus, the present invention provides compositions and methods of delivering antisense compositions to colon cells only.

The present invention provides a colorectal cancer specific approach in which only colorectal cells are exposed to the active portion of the compound and only colorectal cancer cells are effected by the conjugated compound. The ST receptor binding moiety specifically binds to colorectal cells, including normal colorectal cells, localized colorectal cancer cells and metastasized colorectal cancer cells. Upon binding to these cells, the conjugated compound is internalized and the delivery of the conjugated compound including the antisense portion of the molecule is effected. The presence of the conjugated compound in normal colorectal cells has no effect on such cells because the colorectal cancer-associated gene for which the antisense molecule that makes up the active moiety of the conjugated compound is complementary is not being expressed. However, in colorectal cancer cells, the cancer gene for which the antisense molecule that makes up the active moiety of the conjugated compound is complementary is being expressed. The presence of the conjugated compound in colorectal cancer cells serves to inhibit or prevent transcription or translation of the cancer gene and thereby reduce or eliminate the transformed phenotype.

The invention can be used to combat localized or metastasized colorectal cancer as well as to prevent the emergence of the transformed phenotype. Thus the invention can be used therapeutically as well as prophylactically.

Therapeutic and prophylactic pharmaceutical compositions of the present invention include conjugated compounds specifically targeted to colon cells. These conjugated compounds include ST receptor binding moieties which do not bind to cells of normal tissue in the body except cells of the intestinal tract since the cells of other tissues do not possess ST receptors. Thus, only normal colorectal cells, localized colorectal cancer cells and metastasized colorectal cancer cells take up the conjugated compositions.

One having ordinary skill in the art can readily identify individuals suspected of suffering from colorectal cancer and metastasized colorectal cells. In those individuals diagnosed with colorectal cancer, it is standard therapy to suspect metastasis and aggressively attempt to eradicate metasasized cells. The present invention provides pharmaceutical compositions and methods for specifically targeting and eliminating metastasized colorectal cancer cells. Further, the present invention provides pharmaceutical compositions that comprise therapeutics and methods for specifically eliminating colorectal cancer cells. The present invention provides pharmaceutical compositions and methods for specifically in colorectal cells and preventing transformation by such cells by prophylactically furnishing such cells with antisense molecules that inhibit transcription or translation of genes involved in transformation.

The pharmaceutical compositions which comprise conjugated compositions of the present invention may be used to diagnose or treat individuals suffering from localized and/or metastatic colorectal tumors, that is primary or non-metastatic colorectal tumors as well as metastasized colorectal tumors.

The present invention relies upon the use of an ST receptor binding moiety in a conjugated composition. The ST receptor binding moiety is essentially a portion of the conjugated composition which acts as a ligand to the ST receptor and thus specifically binds to these receptors. The conjugated composition also includes an active moiety which is associated with the ST receptor binding moiety; the active moiety being an antisense composition useful to inhibit or prevent transcription or translation of expression of genes whose expression is associated with cancer.

According to the present invention, the ST receptor binding moiety is the ST receptor ligand portion of a conjugated composition. In some embodiments, the ST receptor ligand may be native ST. Native ST has been isolated from a variety of organisms including E. coli, Yersinia, Enterobacter, and others. In nature, the toxins are generally encoded on a plasmid which can "jump" between different species. Several different toxins have been reported to occur in different species. These toxins all possess significant sequence homology, they all bind to ST receptors and they all activate guanylate cyclase, producing diarrhea.

ST has been both cloned and synthesized by chemical techniques. The cloned or synthetic molecules exhibit binding characteristics which are similar to native ST. Native ST isolated from E. coli is 18 or 19 amino acids in length. The smallest "fragment" of ST which retains activity is the 13 amino acid core peptide extending toward the carboxy terminal from cysteine 6 to cysteine 18 (of the 19 amino acid form). Analogues of ST have been generated by cloning and by chemical techniques. Small peptide fragments of the native ST structure which include the structural determinant that confers binding activity may be constructed. Once a structure is identified which binds to ST receptors, non-peptide analogues mimicking that structure in space are designed.

SEQ ID NO:1 discloses a nucleotide sequence which encodes 19 amino acid ST, designated ST Ia, reported by So and McCarthy (1980) Proc. Natl. Acad. Sci. USA 77:4011, which is hereby incorporated herein by reference.

The amino acid sequence of ST Ia is disclosed in SEQ ID NO:2.

SEQ ID NO:3 discloses the amino acid sequence of an 18 amino acid peptide which exhibits ST activity, designated ST I*, reported by Chan and Giannella (1981) J. Biol. Chem. 256:7744, which is hereby incorporated herein by reference.

SEQ ID NO:4 discloses a nucleotide sequence which encodes 19 amino acid ST, designated ST Ib, reported by Mosely et al. (1983) Infect. Immun. 39:1167, which is hereby incorporated herein by reference.

The amino acid sequence of ST Ib is disclosed in SEQ ID NO:5.

A 15 amino acid peptide called guanylin which has about 50% sequence homology to ST has been identified in mammalian intestine (Currie, M. G. et al. (1992) Proc. Natl. Acad Sci. USA 89:947–951, which is hereby incorporated herein by reference). Guanylin binds to ST receptors and activates guanylate cyclase at a level of about 10- to 100-fold less than native ST. Guanylin may not exist aE a 15 amino acid peptide in the intestine but rather as part of a larger protein in that organ. The amino acid sequence of guanylin from rodent is disclosed as SEQ ID NO:6.

SEQ ID NO:7 is an 18 amino acid fragment of SEQ ID NO:2. SEQ ID NO:8 is a 17 amino acid fragment of SEQ ID NO:2. SEQ ID NO:9 is a 16 amino acid fragment of SEQ ID NO:2. SEQ ID NO:10 is a 15 amino acid fragment of SEQ ID NO:2. SEQ ID NO:11 is a 14 amino acid fragment of SEQ ID NO:2. SEQ ID NO:12 is a 13 amino acid fragment of SEQ ID NO:2. SEQ ID NO:13 is an 18 amino acid fragment of SEQ ID NO:2. SEQ ID NO:14 is a 17 amino acid fragment of SEQ ID NO:2. SEQ ID NO:15 is a 16 amino acid fragment of SEQ ID NO:2. SEQ ID NO:16 is a 15 amino acid fragment of SEQ ID NO:2. SEQ ID NO: 17 is a 14 amino acid fragment of SEQ ID NO:2.

SEQ ID NO:18 is a 17 amino acid fragment of SEQ ID NO:3. SEQ ID NO:19 is a 16 amino acid fragment of SEQ ID NO:3. SEQ ID NO:20 is a 15 amino acid fragment of SEQ ID NO:3. SEQ ID NO:21 is a 14 amino acid fragment of SEQ ID NO:3. SEQ ID NO:22 is a 13 amino acid fragment of SEQ ID NC:3. SEQ ID NO:23 is a 17 amino acid fragment of SEQ ID NO:3. SEQ ID NO:24 is a 16 amino acid fragment of SEQ ID NO:3. SEQ ID NO:25 is a 15 amino acid fragment of SEQ ID NO:3. SEQ ID NO:26 is a 14 amino acid fragment of SEQ ID NO:3.

SEQ ID NO:27 is an 18 amino acid fragment of SEQ ID NO:5. SEQ ID NO:28 is a 17 amino acid fragment of SEQ ID NO:5. SEQ ID NO:29 is a 16 amino acid fragment of SEQ ID NO:5. SEQ ID NO:30 is a 15 amino acid fragment of SEQ ID NO:5. SEQ ID NO:31 is a 14 amino acid fragment of SEQ ID NO:5. SEQ ID NO:32 is a 13 amino acid fragment of SEQ ID NO:5. SEQ ID NO:33 is an 18 amino acid fragment of SEQ ID NO:5. SEQ ID NO:34 is a 17 amino acid fragment of SEQ ID NO:5. SEQ ID NO:35 is a 16 amino acid fragment of SEQ ID NO:5. SEQ ID NO:36 is a 15 amino acid fragment of SEQ ID NO: 5. SEQ ID NO:37 is a 14 amino acid fragment of SEQ ID NO:5.

SEQ ID NO:27, SEQ ID NO:31, SEQ ID NO:36 AND SEQ ID NO:37 are disclosed in Yoshimura, S., et al. (1985) FEBS Lett. 181:138, which is hereby incorporated herein by reference.

SEQ ID NO:38, SEQ ID NO:39 and SEQ ID NO:40, which are derivatives of SEQ ID NO:3, are disclosed in.Waldman, S. A. and O'Hanley, P. (1989) Infect. Immun. 57:2420, which is hereby incorporated herein by reference.

SEQ ID NO:41, SEQ ID NO:42, SEQ ID NO:43, SEQ ID NO:44 and SEQ ID NO:45, which are a derivatives of SEQ ID NO:3, are disclosed in Yoshimura, S., et al. (1985) FEBS Lett. 181:138, which is hereby incorporated herein by reference.

SEQ ID NO:46 is a 25 amino acid peptide derived from Y. enterocolitica which binds to the ST receptor.

SEQ ID NO:47 is a 16 amino acid peptide derived from V. choierae which binds to the ST receptor. SEQ ID NO:47 is reported in Shimonishi, Y., et al. FEBS Lett. 215:165, which is hereby incorporated herein by reference.

SEQ ID NO:48 is an 18 amino acid peptide derived from Y. enterocolitica which binds to the ST receptor. SEQ ID NO:48 is reported in Okamoto, K., et al. Infec. Immun. 55:2121, which is hereby incorporated herein by reference.

SEQ ID NO:49, is a derivative of SEQ ID NO:5.

SEQ ID NO:50, SEQ ID NO:51, SEQ ID NO:52 and SEQ ID NO:53 are derivatives.

SEQ ID NO:54 is the amino acid sequence of guanylin from human.

In some preferred embodiments, conjugated compounds comprise ST receptor binding moieties that comprise amino acid sequences selected from the group consisting of SEQ ID NO:2, SEQ ID NO:3, SEQ ID NOS:5–54 and fragments and derivatives thereof.

Those having ordinary skill in the art can readily design and produce derivatives having substantially identical amino acid sequences of ST peptides with deletions and/or insertions and/or conservative substitutions of amino acids. For example, following what are referred to as Dayhof's rules for amino acid substitution (Dayhof, M. D. (1978) Nat. Biomed. Res. Found., Washington, D.C. Vol. 5, supp. 3), amino acid residues in a peptide sequence may be substituted with comparable amino acid residues. Such substitutions are well-known and are based the upon charge and structural characteristics of each amino acid. Derivatives include fragments of ST receptor binding peptides with deletions and/or insertions and/or conservative substitutions.

In some embodiments, ST receptor binding peptides comprise D amino acids. As used herein, the term "D amino acid peptides" is meant to refer to ST receptor binding peptides, fragments or derivatives which comprise at least one and preferably a plurality of D amino acids which are capable of binding to the ST receptor. The use of D amino acid peptides is desirable as they are less vulnerable to degradation and therefore have a longer half-life. D amino acid peptides comprising mostly all or consisting of D amino acids may comprise amino acid sequences in the reverse order of ST receptor binding peptides which are made up of L amino acids.

In some embodiments, ST receptor binding peptides, including D amino acid peptides, are conformationally restricted to present and maintain the proper structural conformation for binding to the ST receptor. The compositions may comprise additional amino acid residues required to achieve proper three dimensional conformation including residues which facilitate circularization or desired folding.

It is preferred that the ST receptor ligand used as the ST receptor binding moiety be as small as possible. Thus it is preferred that the ST receptor ligand be a non-peptide small molecule or small peptide, preferably less than 25 amino acids, more preferably less than 20 amino acids. In some embodiments, the ST receptor ligand which constitute the ST receptor binding moiety of a conjugated composition is less than 15 amino acids. ST receptor binding peptide comprising less than 10 amino acids and ST receptor binding peptide less than 5 amino acids may be used as ST binding moieties according to the present invention. In some embodiments, the ST receptor ligand which constitute the ST receptor binding moiety of a conjugated composition is 10–25 amino acids. In some embodiments, the ST receptor ligand which constitute the ST receptor binding moiety of a conjugated composition is 13–25 amino acids. In some embodiments, the ST receptor ligand which constitute the ST receptor binding moiety of a conjugated composition is 10–20 amino acids. In some embodiments, the ST receptor ligand which constitute the ST receptor binding moiety of a conjugated composition is 13–20 amino acids. In some embodiments, the ST receptor ligand which constitute the ST receptor binding moiety of a conjugated composition is 10, 11, 12, 13, 14, 15, 16, 17, 18, 19, 20, 21, 22, 23, 24 or 25 amino acids. It is within the scope of the present invention to include larger molecules which serve as ST receptor binding moieties including, but not limited to molecules such as antibodies, FAbs and F(Ab)2s which specifically bind to ST receptor.

An assay may be used to test both peptide and non-peptide compositions to determine whether or not they are ST receptor ligands or, to test conjugated compositions to determine if they possess ST receptor binding activity. Such compositions that specifically bind to ST receptors can be identified by a competitive binding assay. The competitive binding assay is a standard technique in pharmacology which can be readily performed by those having ordinary skill in the art using readily available starting materials. Competitive binding assays, ST receptor binding assays, have been shown to be effective for identifying compositions that specifically bind to ST receptors. Briefly, the assay consists of incubating a preparation of ST receptors (e.g. intestinal membranes from rat intestine, human intestine, T84 cells) with a constant concentration ($1 \times 10^{-10}$ M to $5 \times 10^{-10}$ M) of $^{125}$I-ST (any ST receptor ligand such as native STs SEQ ID NO:2, SEQ ID NO:3 or SEQ ID NO:5 may be used) and a known concentration of a test compound. As a control, a duplicate preparation of ST receptors are incubated with a duplicate concentration of $^{125}$I-ST in the absence of test compound. Assays are incubated to equilibrium (2 hours) and the amount of $^{125}$I-ST bound to receptors is quantified by standard techniques. The ability of the test compound to bind to receptors is measured as its ability to prevent (compete with) the $^{125}$I-ST from binding. Thus, in assays containing the test compound which bind to the receptor, there will be less radioactivity associated with the receptors. This assay, which is appropriate for determining the ability of any molecule to bind to ST receptors, is a standard competitive binding assay which can be readily employed by those having ordinary skill in the art using readily available starting materials.

ST may be isolated from natural sources using standard techniques. Additionally, ST receptor binding peptides and conjugated compositions or portions thereof which are peptides may be prepared routinely by any of the following known techniques.

ST receptor binding peptides and conjugated compositions or portions thereof which are peptides may be prepared using the solid-phase synthetic technique initially described by Merrifield, in *J. Am. Chem. Soc.*, 15:2149–2154 (1963). Other peptide synthesis techniques may be found, for example, in M. Bodanszky et al., (1976) *Peptide Synthesis*, John Wiley & Sons, 2d Ed.; Kent and Clark-Lewis in *Synthetic Peptides in Biology and Medicine*, p. 295–358, eds. Alitalo, K., et al. Science Publishers, (Amsterdam, 1985); as well as other reference works known to those skilled in the art. A summary of peptide synthesis techniques may be found in J. Stuart and J. D. Young, *Solid Phase Peptide Synthelia*, Pierce Chemical Company, Rockford, Ill. (1984), which is hereby incorporated herein by reference. The synthesis of peptides by solution methods may also be used, as described in *The Proteins*, Vol. II, 3d Ed., p. 105–237, Neurath, H. et al., Eds., Academic Press, New York, N.Y. (1976). Appropriate protective groups for use in such syntheses will be found in the above texts, as well as in J. F. W. McOmie, *Protective Groups in Organic Chemistry*, Plenum Press, New York, N.Y. (1973), which is hereby incorporated herein by reference. In general, these synthetic methods involve the sequential addition of one or more amino acid residues or suitable protected amino acid residues to a growing peptide chain. Normally, either the Frnino or carboxyl group of the first amino acid residue is protected by a suitable, selectively removable protecting group. A different, selectively removable protecting group is utilized for amino acids containing a reactive side group, such as lysine.

Using a solid phase synthesis as an example, the protected or derivatized amino acid is attached to an inert solid support through its unprotected carboxyl or amino group. The protecting group of the amino or carboxyl group is then selectively removed and the next amino acid in the sequence having the complementary (amino or carboxyl) group suitably protected is admixed and reacted with the residue already attached to the solid support. The protecting group of the amino or carboxyl group is then removed from this newly added amino acid residue, and the next amino acid (suitably protected) is then added, and so forth. After all the desired amino acids have been linked in the proper sequence, any remaining terminal and side group protecting groups (and solid support) are removed sequentially or concurrently, to provide the final peptide. The peptide of the invention are preferably devoid of benzylated or methylbenzylated amino acids. Such protecting group moieties may be used in the course of synthesis, but they are removed before the peptides are used. Additional reactions may be necessary, as described elsewhere, to form intramolecular linkages to restrain conformation.

ST receptor binding peptides and conjugated compositions or portions thereof which are peptides may also be prepared by recombinant DNA techniques. Provision of a suitable DNA sequence encoding the desired peptide permits the production of the peptide using recombinant techniques now known in the art. The coding sequence can be obtained from natural sources or synthesized or otherwise constructed using widely available starting materials by routine methods. When the coding DNA is prepared synthetically, advantage can be taken of known codon preferences of the intended host where the DNA is to be expressed.

To produce an ST receptor binding peptide which occurs in nature, one having ordinary skill in the art can, using well-known techniques, obtain a DNA molecule encoding the ST receptor binding peptides from the genome of the organism that produces the ST receptor binding peptide and insert that DNA molecule into a commercially available expression vector for use in well-known expression systems.

For example, the commercially available plasmid pSE420 (Invitrogen, San Diego, Calif.) may be used for recombinant production in *E. coli*. The commercially available plasmid pYES2 (Invitrogen, San Diego, Calif.) may be used for production in *S. cerevisiae* strains of yeast. The commercially available MaxBac™ (Invitrogen, San Diego, Calif.) complete baculovirus expression system may be used for production in insect cells. The commercially available plasmid pcDNA I (Invitrogen, San Diego, Calif.) may be used for production in mammalian cells such as Chinese Hamster Ovary cells.

One having ordinary skill in the art may use these or other commercially available expression vectors and systems or produce vectors using well-known methods and readily available starting materials. Expression systems containing the requisite control sequences, such as promoters and polyadenylation signals, and preferably enhancers, are readily available and known in the art for a variety of hosts. See e.g., Sambrook et al., *Molecular Cloning a Laboratory Manual*, Second Ed. Cold Spring Harbor Press (1989). Thus, the desired proteins can be prepared in both prokaryotic and eukaryotic systems, resulting in a spectrum of processed forms of the protein.

The most commonly used prokaryotic system remains *E. coli*, although other systems such as *B. subtilis* and Pseudomonas are also useful. Suitable control sequences for prokaryotic systems include both constitutive and inducible promoters including the lac promoter, the trp promoter, hybrid promoters such as tac promoter, the lambda phage Pl promoter. In general, foreign proteins may be produced in these hosts either as fusion or mature proteins. When the desired sequences are produced as mature proteins, the sequence produced may be preceded by a methionine which is not necessarily efficiently removed. Accordingly, the peptides and proteins claimed herein may be preceded by an N-terminal Met when produced in bacteria. Moreover, constructs may be made wherein the coding sequence for the peptide is preceded by an operable signal peptide which results in the secretion of the protein. When produced in prokaryotic hosts in this matter, the signal sequence is removed upon secretion.

A wide variety of eukaryotic hosts are also now available for production of recombinant foreign proteins. As in bacteria, eukaryotic hosts may be transformed with expression systems which produce the desired protein directly, but more commonly signal sequences are provided to effect the secretion of the protein. Eukaryotic systems have the additional advantage that they are able to process introns which may occur in the genomic sequences encoding proteins of higher organisms. Eukaryotic systems also provide a variety of processing mechanisms which result in, for example, glycosylation, carboxy-terminal amidation, oxidation or derivatization of certain amino acid residues, conformational control, and so forth.

Commonly used eukaryotic systems include, but are not limited to, yeast, fungal cells, insect cells, mammalian cells, avian cells, and cells of higher plants. Suitable promoters are available which are compatible and operable for use in each of these host types as well as are termination sequences and enhancers, as e.g. the baculovirus polyhedron promoter. As above, promoters can be either constitutive or inducible. For example, in mammalian systems, the mouse metallothionene promoter can be induced by the addition of heavy metal ions.

The particulars for the construction of expression systems suitable for desired hosts are known to those in the art. For recombinant production of the protein, the DNA encoding it is suitably ligated into the expression vector of choice and then used to transform the compatible host which is then cultured and maintained under conditions wherein expression of the foreign gene takes place. The protein of the present invention thus produced is recovered from the culture, either by lysing the cells or from the culture medium as appropriate and known to those in the art.

One having ordinary skill in the art can, using well-known techniques, isolate the protein that is produced.

According to the present invention, the active moiety is an antisense composition. In particular, the antisense molecule that makes up the active moiety of a conjugated compound hybridizes to DNA or RNA in a colon cell and inhibits and/or prevents transcription or translation of the DNA or RNA from taking place. The antisense compositions may be a nucleic acid molecule, a derivative or an analogs thereof. The chemical nature of the antisense composition may be that of a nucleic acid molecule or a modified nucleic acid molecule or a non-nucleic acid molecule which possess functional groups that mimic a DNA or RNA molecule that is complementary to the DNA or RNA molecule whose expression is to be inhibited or otherwise prevented. Antisense compositions inhibit or prevent transcription or translation of genes whose expression is linked to colorectal cancer, i.e. colorectal cancer associated genes. Examples of such genes include, but are not limited to: hereditary nonpolyposis coli (HNPCC) genes such as hMSH2, hMLH1, hPMS1, and hPMS2, Ras, adenomatous polyposis coli (APC), ERBB-1/HER-1, ERBB-2/HER-2, p53 Tumor Suppressor, MYB, FOS, ABL, MYC, Protein Tyrosine Phosphatase G1, Cyclic AMP-Dependent Protein Kinase (PKA), CRIPTO, Transforming Growth Factor Alpha and 1p.

Colorectal cancer-associated genes provide the genetic basis for colorectal cancer. Colorectal cancer is a process involving accumulation of genetic mutations in epithelial cells leading to the neoplastic phenotype associated with unregulated growth. Colorectal carcinogenesis is a multistage process involving the progression from adenomas to invasive carcinomas. Indeed, the cumulative total of genetic abnormalities appear to be more important than their order of appearance. Many of the genetic abnormalities result from allelic loss or deletion of fragments of chromos-mes. Specific genetic abnormalities which have been associated with the colorectal cancer phenotype will be discussed below. These all are potential s for treatment employing genetic approaches. See: Toribara, N W and Sleisenger, M H (1995) Screening for colorectal cancer. *New Eng. J. Med.* 332:861–867 which is hereby incorporated herein by reference including all references cited therein which are also hereby incorporated herein by reference.

HNPCC refers to 4 genes that are suspected to be responsible for hereditary nonpolyposis coli (HNPCC) colorectal cancer. These four genes have been identified and are discussed in Toribara, N W and Sleisenger, M H (1995) Screening for colorectal cancer. *New Eng. J. Med.* 332:861–867. The genes, called hMSH2, hMLH1, hPMS1, and hPMS2, are proofreading genes that repair mismatches of bases in DNA. Loss of this function allows replication errors to occur in the DNA.

Point mutations insertions, and deletions in K-ras and H-ras have been identified in colorectal tumors. See: Toribara, N W and Sleisenger, M H (1995) Screening for colorectal cancer. *New Eng. J. Med.* 332:861–867; Kniazev, P G, et al. Complex characteristics of the alterations of oncogenes HER-2/ERBB-2, HER-1/ERBB-1, HRAS-1, C-MYC and anti-oncogenes p53, RB1, as well as deletions of loci of chromosome 17 in colon carcinoma. *Molekuliarnaia Biologiia*. 26(5):1134–47, 1992, September October, and Ramsay, R G, et al. Myb expression is higher in malignant human colonic carcinoma and premalignant adenomatous polyps than in normal mucosa. *Cell Growth & Differentiation*. 3(10):723–30, 1992 October, which are each hereby incorporated herein by reference including all references cited therein which are also hereby incorporated herein by reference.

Patients with familial adenomatous polyposis coli (APC) appear to have a series of deletions including deletions of chromosome 5q, 18q, 17p. The 17p deletion represents a deletion of the p53 suppressor gene.

ERBB-1/HER-1 and ERBB-2/HER-2 genes have been demonstrated to be amplified in about 4–8% of cases of colorectal cancer.

Point mutations in p53 genes have been reported to be mutated in about 3% of colorectal cancer cases.

MYB proto-oncogene expression has been demonstrated to be higher in colorectal tumors. See: Ramsay, R G, Thompson, M A, Hayman, J A, Reid, G, Gonda, T J, Whitehead, R H Myb expression is higher in malignant human colonic carcinoma and premalignant adenomatous polyps than in normal mucosa. *Cell Growth & Differentiation*. 3(10):723–30, 1992 October; Melani, C. et al. Inhibition of proliferation by c-myb antisense oligodeoxynucleotides in colon adenocarcinoma cell lines that express c-myb. *Cancer Research* 51(11):2897–901, Jun 1, 1991; and Ramsay R G, et al. Myb expression is higher in malignant human colonic carcinoma and premalignant adenomatous polyps than in normal mucosa. *Cell Growth & Differentiation*. 3(10):723–30, 1992 October; which are each hereby incorporated herein by reference including all references cited therein which are also hereby incorporated herein by reference. Indeed, tumors and cells with the highest levels of expression of MYB were the most dysplastic and had the highest levels of proliferation. cMYB is a protooncogene which plays a role in the proliferation signaling pathway. Rearrangements, insertions, and deletions of this gene have been observed. See: Alexander, R. J, et al. oncogene alterations in rat colon tumors induced by N-methyl-N-nitrosourea. *American Journal of the Medical Sciences*. 303(1):16–24, 1992, January which is hereby incorporated herein by reference including all references cited therein which are also hereby incorporated herein by reference. Antisense MYB oligonucleotides retard the proliferation of colonic adenocarcinoma cells which had the highest level of expression of this oncogene, in vitro.

Chemical carcinogenesis in a rat model demonstrated point mutations in fos, an oncogene which mediates transcriptional regulation and proliferation. See: Alexander, R J, et al. Oncogene alterations in rat colon tumors induced by N-methyl-N-nitrosourea. *American Journal of the Medical Sciences*. 303(1):16–24, 1992, January which is hereby incorporated herein by reference including all references cited therein which are also hereby incorporated herein by reference.

Chemical carcinogenesis in a rat model demonstrated point mutations in the oncogene abl. See: Alexander, R J, et al. Oncogene alterations in rat colon tumors induced by N-methyl-N-nitrosourea. *American Journal of the Medical Sciences*. 303(1):16–24, 1992, January.

MYC is an oncogene that plays a role in regulating transcription and proliferation. Increased expression of MYC has been found in colorectal cancer cells. Collins, J F, et al. c-myc antisense oligonucleotides inhibit the colony-forming capacity of Colo 320 colonic carcinoma cells. *Journal of Clinical Investigation*. 89 (5):1523–7, 1992 May.; and Rodriguez-Alfageme, C, et al. Suppression of deregulated c-MYC expression in human colon carcinoma cells by chromosome 5 transfer. *Proceedings of the National Academy of Sciences of the United States of America*. 89(4):1482–6, Feb. 15, 1992 which are both hereby incorporated herein by reference including all references cited therein which are also hereby incorporated herein by reference. A 15-base antisense oligonucleotide to myc complementary to the translation initiation region of exon II was incubated with colorectal cancer cells. This antisense molecule inhibited proliferation of colorectal cancer cells in a dos-dependent fashion. Interestingly, the uptake of this oligonucleotide was low (0.7%). Also, transfer of a normal chromosome 5 to colorectal cancer cells resulted in the regulation of myc expression and loss of proliferation. These data suggest that a tumor suppressor gene important in the regulation of myc is contained on this chromosome.

A novel protein tyrosine phosphatase, G1, has been identified. Examination of the mRNA encoding this protein in colorectal tumor cells revealed that it undergoes point mutations and deletions in these cells and may play a role in proliferation characteristic of these cells. Takekawa, M. et al. Chromosomal localization of the protein tyrosine phosphatase G1 gene and characterization of the aberrant transcripts in human colon cancer cells. *FEBS Letters*. 339(3):222–8, Feb. 21, 1994 which is hereby incorporated herein by reference including all references cited therein which are also hereby incorporated herein by reference.

Gastrin regulates colon cancer cell growth through a cyclic AMP-dependent mechanism mediated by PKA. Antisense oligodeoxynucleotides to the regulatory subunit of a specific class of PKA inhibited the growth-promoting effects of cyclic AMP in colon carcinoma cells. See: Bold, R J, et al. Experimental gene therapy of human colon cancer. *Surgery*. 116(2):189–95; discussion 195–6, 1994 August and Yokozaki, H., et al. An antisense oligodeoxynucleotide that depletes RI alpha subunit of cyclic AMP-dependent protein kinase induces growth inhibition in huran cancer cells. *Cancer Research*. 53(4):868–72, Feb. 15, 1993 which are both hereby incorporated herein by reference including all references cited therein which are also hereby incorporated herein by reference.

CRIPTO is an epidermal growth factor-related gene expressed in a majority of colorectal cancer tumors. Antisense phosphorothioate oligodeoxynucleotides to the 5'-end of CRIPTO mRNA significantly reduced CRIPTO expression and inhibited colorectal tumor cell growth in vitro and in vivo. Ciardiello, F. et al. Inhibition of CRIPTO expression and tumorigenicity in human colon cancer cells by antisense RNA and oligodeoxynucleotides. *Oncogene*. 9(1):291–8, 1994 January which are both hereby incorporated herein by reference including all references cited therein which are also hereby incorporated herein by reference.

Many carcinoma cells secrete transforming growth factor alpha. A 23 nucleotide antisense oligonucleotide to TGF alpha mRNA inhibited both DNA synthesis an proliferation of colorectal cancer cells. Sizeland, A. M, Burgess, A. W.

Antisense transforming growth factor alpha oligonucleotides inhibit autocrine stimulated proliferation of a colon carcinoma cell line. *Molecular Biology of the Cell.* 3 (11):1235–43, 1992 November which is hereby incorporated herein by reference including all references cited therein which are also hereby incorporated herein by reference.

Human colorectal tumors have been identified with deletions of chromosome 1p. It appears that a portion of this chromosome, 1p36–34, contains a tumor suppressor gene that regulates the expression of MYC. Tanaka, K, et al. Suppression of tumorigenicity in human colon carcinoma cells by introduction of normal chromosome 1p36 region. *Oncogene.* 8(8):2253–8, 1993 August, which is hereby incorporated herein by reference including all references cited therein which are also hereby incorporated herein by reference.

Antisense compositions including oligonucleotides, derivatives and analogs thereof, conjugation protocols, and antisense strategies for inhibition of transcription and translation are generally described in: *Antisense Research and Applications,* Crooke, S. and B. Lebleu, eds. CRC Press, Inc. Boca Raton Fla. 1993; *Nucleic Acids in Chemistry and Biology* Blackburn, G. and M. J. Gait, eds. IRL Press at Oxford University Press, Inc. New York 1990; and *Oligonucleotides and Analogues: A Practical Approach* Eckstein, F. ed., IRL Press at Oxford University Press, Inc. New York 1991; which are each hereby incorporated herein by reference including all references cited therein which are hereby incorporated herein by reference.

The antisense molecules of the present invention comprise a sequence complementary to a fragment of a colorectal cancer gene. See Ullrich et al., *EMBO J.*, 1986, 5:2503, which is hereby incorporated herein by reference. Contemplated by this definition are fragments of oligos within the coding sequence of colorectal cancer genes.

Antisense compositions which can make up an active moiety in conjugated compounds of the invention include oligonucleotides formed of homopyrimidines can recognize local stretches of homopurines in the DNA double helix and bind to them in the major groove to form a triple helix. See: Helen, C and Toulme, J J. Specific regulation of gene expression by antisense, sense, and antigene nucleic acids. *Biochem. Biophys Acta*, 1049:99–125, 1990 which is hereby incorporated herein by reference including all references cited therein which are hereby incorporated herein by reference. Formation of the triple helix would interrupt the ability of the specific gene to undergo transcription by RNA polymerase. Triple helix formation using myc-specific oligonucleotides has been observed. See: Cooney, M, et al. *Science* 241:456–459 which is hereby incorporated herein by reference including all references cited therein which are hereby incorporated herein by reference.

Antisense oligonucleotides of DNA or RNA complementary to sequences at the boundary between introns and exons can be employed to prevent the maturation of newly-generated nuclear RNA transcripts of specific yenes into mRNA for transcription.

Antisense RNA complimentary to specific genes can hybridize with the mRNA for tat gene and prevent its translation. Antisense RNA can be provided to the cell as "ready-to-use" RNA synthesized in vitro or as an antisense gene stably transfected into cells which will yield antisense RNA upon transcription. Hybridization with mRNA results in degradation of the hybridized molecule by RNAse H and/or inhibition of the formation of translation complexes. Both result in a failure to produce the product of the original gene.

Antisense sequences of DNA or RNA can be delivered to cells. Several chemical modifications have been developed to prolong the stability and improve the function of these molecules without interfering in their ability to recognize specific sequences. These include increasing their resistance to degradation by DNases, including phosphotriesters, methylphosphonates, phosphorothioates, alpha-anomers, increasing their affinity for their s by covalent linkage to various intercalating agents such as psoralens, and increasing uptake by cells by conjugation to various groups including polylysine. These molecules recognize specific sequences encoded in mRNA and their hybridization prevents translation of and increases the degradation of these messages.

Conjugated compositions of the invention provide a specific and effective means for terminating the expression of genes which cause neoplastic transformation. ST receptors undergo ligand-induced endocytosis and can deliver conjugated compounds to the cytoplasm of cells when the ST receptor binding moiety binds to an ST receptor on a colon cell. The unique localization of these receptors and their ability to undergo endocytosis make them excellent candidates for targeting therapeutics to these tumors.

ST receptor binding moieties are conjugated directly to antisense compositions such as nucleic acids which are active in inducing a response in colorectal tumor cells. For example, antisense oligonucleotides to MYC are conjugated directly to ST. This has been performed employing peptides that bind to the CD4 receptor. See: Cohen, J S, ed. Oligodeoxynucleotides: *Antisense Inhibitors of Gene Expression. Topics in Molecular and Structural Biology.* CRC Press, Inc., Boca Raton, 1989. which is hereby incorporated herein by reference including all references cited therein which are hereby incorporated herein by reference. The precise backbone and its synthesis is not specified and can be selected from well-established techniques. Synthesis would involve either chemical conjugation or direct synthesis of the chimeric molecule by solid phase synthesis employing FMOC chemistry. See: Haralambidis, J, et al. (1987) *Tetrahedron Lett.* 28:5199–5202, which is hereby incorporated herein by reference including all references cited therein which are hereby incorporated herein by reference. Alternatively, the peptide-nucleic acid conjugate may be synthesized directly by solid phase synthesis as a peptide-peptide nucleic acid chimera by solid phase synthesis. Nielsen, P. E, et al. (1994) Sequence-specific transcription arrest by peptide nucleic acid bound to the DNA template strand. *Gene* 149:139–145, which is hereby incorporated herein by reference including all references cited therein which are hereby incorporated herein by reference. Also, ST may be chemically coupled directly to the peptide nucleic acid employing established chemistry.

In some embodiments, polylysine can be complexed to conjugated compositions of the invention in a non-covalent fashion to nucleic acids and used to enhance delivery of these molecules to the cytoplasm of cells. In addition, peptides and proteins can be conjugated to polylysine in a covalent fashion and this conjugate complexed with nucleic acids in a non-covalent fashion to further enhance the specificity and efficiency of uptake of the nucleic acids into cells. Thus, ST binding peptide is conjugated chemically to polylysine by established techniques. The polylysine-ST conjugate may be complexed with nucleic acids of choice. Thus, polylysine-orosomucoid conjugates were employed to specifically plasmids containing genes to be expressed to hepatoma cells expressing the orosomucoid receptor. This approach can be used to delivery whole genes, or oligonucleotides. Thus, it has the potential to terminate the expression of an undesired gene (eg. MYC, ras) or replace the function of a lost or deleted gene (eg. hMSH2, hMLH1, hPMS1, and hPMS2).

According to a preferred embodiment, Myc serves as a gene whose expression is inhibited by an antisense molecule within a conjugated composition. Many, if not most, colorectal tumor cells overexpress MYC, a gene involved in mediating proliferation. Decreasing the proliferation of colorectal tumor cells is attained by employing antisense oligonucleotides complimentary to MYC to hybridize with the mRNA for this protein, resulting in the degradation of this message and a dramatic reduction in the production of MYC. ST receptor biding moieties are used to a 15-based antisense oligonucleotide to myc complementary to the translation initiation region of exon II. This construct was active in inhibiting the expression of MYC when it was incubated with colorectal cancer cells. The 15-base antisense oligonucleotide to MYC is synthesized as reported in Collins, J F, Herman, P, Schuch, C, Bagby G C, Jr. *Journal of Clinical Investigation.* 89(5):1523–7, 1992 May. In some embodiments, the conjugated composition is conjugated to polylysine as reported previously. Wu, G Y, and Wu, C H. (1988) Evidence for ed gene delivery to Hep G2 hepatoma cells in vitro. *Biochem.* 27:887–892 which is incorporated herein by reference.

Conjugated compositions may be synthesized as a chimeric molecule directly by solid phase synthesis. pmolar to nanomolar concentrations for this conjugate suppress MYC synthesis in colorectal cancer cells in vitro.

Antisense molecules are preferably hybridize to, i.e. are complementary to, a nucleotide sequence that is 5–50 nucleotides in length, more preferably 5–25 nucleotides and in some embodiments 10–15 nucleotides.

In addition, mismatches within the sequences identified above, which achieve the methods of the invention, such that the mismatched sequences are substantially complementary to the colorectal cancer genie sequences are also considered within the scope of the disclosure. Mismatches which permit substantial complementarity to the colorectal cancer gene sequences will be known to those of skill in the art once armed with the present disclosure. The oligos may also be unmodified or modified.

Therapeutic compositions and methods may be used to combat colorectal cancer in cases where the cancer is localized and/or metastasized. Individuals are administered a therapeutically effective amount of conjugated compound. A therapeutically effective amount is an amount which is effective to cause a cytotoxic or cytostatic effect on metastasized colorectal cancer cells without causing lethal side effects on the individual. An individual who has been administered a therapeutically effective amount of a conjugated composition has a increased chance of eliminating colon cancer as compared to the risk had the individual not received the therapeutically effective amount.

To treat localized colorectal cancer, a therapeutically effective amount of a conjugated compound is administered such that it will come into contact with the localized tumor within the colon. Thus, the conjugated compound is administered orally or rectally. In cases where conjugated compounds are orally administered, they are preferably enteric coated or otherwise formulated to avoid degradation by stomach acids. Enteric formulations are described in U.S. Pat. No. 4,601,896, U.S. Pat. No. 4,729,893, U.S. Pat. No. 4,849,227, U.S. Pat. No. 5,271,961, U.S. Pat. No. 5,350,741, and U.S. Pat. No. 5,399,347, which are each hereby incorporated herein by reference. Oral and rectal formulation are taught in Remington's Pharmaceutical Sciences, 18th Edition, 1990, Mack Publishing Co., Easton Pa. which is incorporated herein by reference. Alternative embodiments include sustained release formulations and implant devices which provide continuous delivery of conjugated compositions to the colon.

Metastasized colorectal tumnors may be treated by systemic administration of conjugated compositions. In some embodiments, routes of administration include those selected from the group consisting of intravenous, intraarterial, intraperitoneal, local administration into the blood supply of the organ in which the tumor resides or directly into the tumor itself. Intravenous administration is the preferred mode of administration. It may be accomplished with the aid of an infusion pump.

Suitable pharmaceutical carriers are described in *Remington's Pharmaceutical Sciences*, A. Osol, a standard reference text in this field, which is incorporated herein by reference. In carrying out methods of the present invention, conjugated compounds of the present invention can be used alone or in combination with other diagnostic, therapeutic or additional agents. Such additional agents include excipients such as coloring, stabilizing agents, osmotic agents and antibacterial agents.

The conjugated compositions of the invention can be, for example, formulated as a solution, suspension or emulsion in association with a pharmaceutically acceptable parenteral vehicle. Examples of such vehicles are water, saline, Ringer's solution, dextrose solution, and 5% human serum albumin. Liposomes may also be used. The vehicle may contain additives that maintain isotonicity (e.g., sodium chloride, mannitol) and chemical stability (e.g., buffers and preservatives). The formulation is sterilized by commonly used techniques. For example, a parenteral composition suitable for administration by injection is prepared by dissolving 1.5% by weight of active ingredient in 0.9% sodium chloride solution.

The pharmaceutical compositions according to the present invention may be administered as either a single dose or in multiple doses. The pharmaceutical compositions of the present invention may be administered either as individual therapeutic agents or in combination with other therapeutic agents. The treatments of the present invention may be combined with conventional therapies, which may be administered sequentially or simultaneously.

The present invention is directed to a method of delivering antisense compounds to colon cells and inhibiting expression of colorectal cancer genes in mammals. The methods comprise administering to a mammal an effective amount of a conjugated composition which comprises an ST receptor binding moiety conjugated to an antisense oligonucleotide having a sequence which is complementary to a region of DNA or mRNA of a colorectal cancer gene.

The conjugated compounds may be administering to mammals in a mixture with a pharmaceutically-acceptable carrier, selected with regard to the intended route of administration and the standard pharmaceutical practice. Dosages will be set with regard to weight, and clinical condition of the patient. The conjugated compositions of the present invention will be administered for a time sufficient for the mammals to be free of undifferentiated cells and/or cells having an abnormal phenotype. In therapeutic methods treatment extends for a time sufficient to inhibit transformed cells from proliferating and conjugated compositions may be administered in conjunction with other chemotherapeutic agents to manage and combat the patient's cancer.

The conjugated compounds of the invention may be employed in the method of the invention singly or in combination with other compounds. The amount to be administered will also depend or such factors as the age, weight, and clinical condition of the patient. See Gennaro, Alfonso, ed., Remington's Pharmaceutical Sciences, 18th Edition, 1990, Mack Publishing Co., Easton Pa.

Prophylactic compositions and methods may be used to prevent the origin of colorectal cancer. In particular, conjugated compounds may be administered to an individual is suspected of being susceptible to colorectal cancer. Using genotyping techniques, the specific nature of an individuals susceptibility may be identified. That is, it may be possible to determine what cancer gene will be associated with colorectal cancer in an individual. For example, defects in the APC gene and kits for diagnosing the same are disclosed in U.S. Pat. No. 5,352,775 which is hereby incorporated herein by reference. Similarly, defects in the MCC gene and kits for diagnosing the same are disclosed in U.S. Pat. No. 5,330,892 which is hereby incorporated herein by reference. In prophylactic methods, treatment extends continuously or sporadically from time to time for a time sufficient to inhibit transformation.

To prevent colorectal cancer, a prophylactically effective amount of a conjugated compound is administered such that it will come into contact with and incorporated by normal colon cells. Thus, the conjugated compound is administered orally or rectally. In cases where conjugated compounds are orally administered, they are preferably enteric coated or otherwise formulated to avoid degradation by stomach acids as described above.

A prophylactically effective amount is an amount which is effective to prevent the initiation of transformation of colon cancer in cells. An individual who has been administered a prophylactically effective amount of a conjugated composition has a reduced risk of development of colon cancer as compared to the risk had the individual not received the prophylactically effective amount.

What is claimed is:

1. A conjugated compound comprising:
a) a ST receptor binding moiety; and,
b) an active moiety;
wherein said active moiety is an antisense molecule.

2. The compound of claim 1 wherein said ST receptor binding moiety is a peptide.

3. The compound of claim 1 wherein said ST receptor binding moiety is selected from the group consisting of: SEQ ID NO:2, SEQ ID NO:3, SEQ ID NOS:5–54 and fragments and derivatives thereof.

4. The compound of claim 1 wherein said ST receptor binding moiety is selected from the group consisting of: SEQ ID NO:2, SEQ ID NO:3, SEQ ID NOS:5–54.

5. The compound of claim 1 wherein said an active moiety is an antisense molecule that hybridizes to nucleotide sequences of DNA or RNA that encode a gene selected from the group consisting of: hereditary nonpolyposis coli (HNPCC) genes such as hMSH2, hMLH1, hPMS1, and hPMS2, Ras, adenomatous polyposis coli (APC), ERBB-1/HER-1, ERBB-2/HER-2, p53 Tumor Suppressor, MYB, FOS, ABL, MYC, Protein Tyrosine Phosphatase G1, Cyclic AMP-Dependent Protein Kinase (PKA), CRIPTO, Transforming Growth Factor Alpha and 1p.

6. The compound of claim 1 wherein said ST receptor binding moiety is selected from the group consisting of: SEQ ID NO:2, SEQ ID NO:3, SEQ ID NOS:5–54 and said an active moiety is an antisense molecule that hybridizes to nucleotide sequences of DNA or RNA that encode a gene selected from the group consisting of: hereditary nonpolyposis coli (HNPCC) genes such as hMSH2, hMLH1, hPMS1, and hPMS2, Ras, adenomatous polyposis coli (APC), ERBB-1/HER-1, ERBB-2/HER-2, p53 Tumor Suppressor, MYB, FOS, ABL, MYC, Protein Tyrosine Phosphatase G1, Cyclic AMP-Dependent Protein Kinase (PKA), CRIPTO, Transforming Growth Factor Alpha and 1p.

7. A pharmaceutical composition comprising:

a) a pharmaceutically acceptable carrier or diluent, and, b) a conjugated compound according to claim 1.

8. The pharmaceutical composition of claim 7 wherein said ST receptor binding moiety is a peptide.

9. The pharmaceutical composition of claim 7 wherein said ST receptor binding moiety is selected from the group consisting of: SEQ ID NO:2, SEQ ID NO:3, SEQ ID NOS:5–54 and fragments and derivatives thereof.

10. The pharmaceutical composition of claim 7 wherein said ST receptor binding moiety is selected from the group consisting of: SEQ ID NO:2, SEQ ID NO:3, SEQ ID NOS:5–54.

11. The pharmaceutical composition of claim 7 wherein said an active moiety is an antisense molecule that hybridizes to nucleotide sequences of DNA or RNA that encode a gene selected from the group consisting of: hereditary nonpolyposis coli (HNPCC) genes such as hMSH2, hMLH1, hPMS1, and hPMS2, Ras, adenomatous polyposis coli (APC), ERBB-1/HER-1, ERBB-2/HER-2, p53 Tumor Suppressor, MYB, FOS, ABL, MYC, Protein Tyrosine Phosphatase G1, Cyclic AMP-Dependent Protein Kinase (PKA) CRIPTO, Transforming Growth Factor Alpha and 1p.

12. The pharmaceutical composition of claim 7 wherein said ST receptor binding moiety is selected from the group consisting of: SEQ ID NO:2, SEQ ID NO:3, SEQ ID NOS:5–54 and said an active moiety is an antisense molecule that hybridizes to nucleotide sequences of DNA or RNA that encode a gene selected from the group consisting of: hereditary nonpolyposis coli (HNPCC) genes such as hMSH2, hMLH1, hPMS1, and hPMS2, Ras, adenomatous polyposis coli (APC), ERBB-1/HER-1, ERBB-2/HER-2, p53 Tumor Suppressor, MYB, FOS, ABL, MYC, Protein Tyrosine Phosphatase G1, Cyclic AMP-Dependent Protein Kinase (PKA), CRIPTO, Transforming Growth Factor Alpha and 1p.

13. The pharmaceutical composition of claim 7 wherein said pharmaceutical composition is an enteric formulation.

14. A method of treating an individual suspected of suffering from colorectal cancer comprising the steps of administering to said individual a therapeutically effective amount of a pharmaceutical composition according to claim 7.

15. The method of claim 14 wherein said pharmaceutical composition is administered orally.

16. The method of claim 14 wherein said pharmaceutical composition is administered intravenously.

17. The method of claim 14 wherein said ST receptor binding moiety is selected from tei group consisting of: SEQ ID NO:2, SEQ ID NO:3, SEQ ID NOS:5–54 and said an active moiety is an antisense molecule that hybridizes to nucleotide sequences of DNA or RNA that encode a gene selected from the group consisting of: hereditary nonpolyposis coli (HNPCC) genes such as hMSH2, hMLH1, hPMS1, and hPMS2, Ras, adenomatous polyposis coli (APC), ERBB-1/HER-1, ERBB-2/HER-2, p53 Tumor Suppressor, MYB, FOS, ABL, MYC, Protein Tyrosine Phosphatase G1, Cyclic AMP-Dependent Protein Kinase (PKA), CRIPTO, Transforming Growth Factor Alpha and 1p.

18. A method of preventing colorectal cancer in an individual suspected of being susceptible to colorectal cancer comprising the steps of administering to said individual a prophylactically effective amount of a pharmaceutical composition according to claim 7.

19. The method of claim 18 wherein said ST receptor binding moiety is selected from the group consisting of: SEQ ID NO:2, SEQ ID NO:3, SEQ ID NOS:5–54 and said an active moiety is an antisense molecule that hybridizes to nucleotide sequences of DNA or RNA that encode a gene selected from the group consisting of: hereditary nonpolyposis coli (HNPCC) genes such as hMSH2, hMLH1, hPMS1, and hPMS2, Ras, adenomatous polyposis coli (APC), ERBB-1/HER-1, ERBB-2/HER-2, p53 Tumor Suppressor, MYB, FOS, ABL, MYC, Protein Tyrosine Phosphatase G1, Cyclic AMP-Dependent Protein Kinase (PKA), CRIPTO, Transforming Growth Factor Alpha and 1p.

* * * * *

UNITED STATES PATENT AND TRADEMARK OFFICE
CERTIFICATE OF CORRECTION

PATENT NO. : 6,087,109
DATED : July 11, 2000
INVENTOR(S) : Waldman

It is certified that error appears in the above-indentified patent and that said Letters Patent is hereby corrected as shown below:

Column 7, line 34, please delete "aE" and insert therefor --as--;

Column 10, line 29, please delete "Frnino" and insert therefor --amino--;

Column 12, line 50, please delete "chromos-mes" and insert therefor --chromosomes--;

Column 17, line 39, please delete "genie" and insert therefor --gene--;

Column 43, line 11, please delete "tei" and insert therefor --the--;

Signed and Sealed this

Twenty-second Day of May, 2001

Attest:

NICHOLAS P. GODICI

Attesting Officer

Acting Director of the United States Patent and Trademark Office